United States Patent
Dhurwasulu et al.

(10) Patent No.: US 9,512,141 B2
(45) Date of Patent: Dec. 6, 2016

(54) PYRAZINE DERIVATIVES AS CB2 RECEPTOR AGONISTS

(71) Applicant: Hoffmann-La Roche Inc., Little Falls, NJ (US)

(72) Inventors: Baledi Dhurwasulu, Andhra Pradesh (IN); Uwe Grether, Efringen-Kirchen (DE); Matthias Nettekoven, Grenzach-Wyhlen (DE); Stephan Roever, Inzlingen (DE); Mark Rogers-Evans, Bottmingen (CH); Tanja Schulz-Gasch, Ziefen (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/648,399

(22) PCT Filed: Dec. 4, 2013

(86) PCT No.: PCT/EP2013/075444
§ 371 (c)(1),
(2) Date: May 29, 2015

(87) PCT Pub. No.: WO2014/086807
PCT Pub. Date: Jun. 12, 2014

(65) Prior Publication Data
US 2015/0299220 A1    Oct. 22, 2015

(30) Foreign Application Priority Data
Dec. 7, 2012 (EP) ..................... 12196024

(51) Int. Cl.

| | | |
|---|---|---|
| *A61K 31/497* | (2006.01) | |
| *C07D 401/14* | (2006.01) | |
| *C07D 403/04* | (2006.01) | |
| *C07D 403/12* | (2006.01) | |
| *C07D 403/14* | (2006.01) | |
| *C07D 413/14* | (2006.01) | |
| *C07D 498/08* | (2006.01) | |
| *C07D 403/06* | (2006.01) | |
| *C07D 413/06* | (2006.01) | |
| *C07D 417/14* | (2006.01) | |
| *C07D 491/107* | (2006.01) | |

(52) U.S. Cl.
CPC ........... *C07D 498/08* (2013.01); *C07D 401/14* (2013.01); *C07D 403/04* (2013.01); *C07D 403/06* (2013.01); *C07D 403/14* (2013.01); *C07D 413/06* (2013.01); *C07D 413/14* (2013.01); *C07D 417/14* (2013.01); *C07D 491/107* (2013.01)

(58) Field of Classification Search
CPC C07D 401/14; C07D 403/04; C07D 403/14; C07D 403/12; C07D 413/14
See application file for complete search history.

(56) References Cited

U.S. PATENT DOCUMENTS

| 2008/0085905 A1 | 4/2008 | Dietz et al. |
| 2012/0065212 A1 | 3/2012 | Hebeisen et al. |
| 2013/0109665 A1* | 5/2013 | Bissantz et al. ............ 514/210.2 |

FOREIGN PATENT DOCUMENTS

| WO | 2008/040649 A2 | 4/2008 |
| WO | 2012/032018 A1 | 3/2012 |
| WO | 2012/168350 A1 | 12/2012 |

OTHER PUBLICATIONS

Dubois et al., "A new pathway to substituted 6-chloro-2-pyridinecarboxylic acid derivatives from the reaction of 4,6-dichloro-2-oxa-5-aza-bicyclo[2.2.2]oct-5-en-3-ones with nucleophiles" Tetrahedron 52(20):6997-7002 (1996).
International Search Report issued in International Application No. PCT/EP2013/075225, dated Jan. 17, 2014 (in 2 pages).
International Search Report issued in International Application No. PCT/EP2013/075442, dated Feb. 17, 2014 (in 2 pages).
International Search Report issued in International Application No. PCT/EP2013/075443, dated Feb. 18, 2014 (in 3 pages).
International Search Report issued in International Application No. PCT/EP2013/075444, dated Jan. 22, 2014 (in 4 pages).
Sammakia et al., "Total Synthesis of Caerulomycin C via the Halogen Dance Reaction" Organic Letters 4(14):2385-2388 (2002).

* cited by examiner

*Primary Examiner* — Brian McDowell
(74) *Attorney, Agent, or Firm* — Alex Andrus

(57) ABSTRACT

The invention relates to a compound of formula (I) wherein $R^1$ to $R^4$ are defined as in the description and in the claims. The compound of formula (I) is a CB2 receptor agonist for use in the treatment of several disorders, such as pain, atherosclerosis and glaucoma.

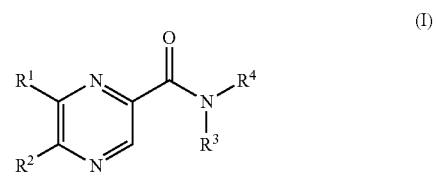

(I)

10 Claims, No Drawings

PYRAZINE DERIVATIVES AS CB2 RECEPTOR AGONISTS

CROSS-REFERENCE TO RELATED APPLICATIONS

This application is a 371 application of International Application No. PCT/EP2013/075444, filed on Dec. 4, 2013, which claims priority to European Patent Application No. 12196024.9, filed on Dec. 7, 2012, the entire contents of which are incorporated herein by reference.

The present invention relates to organic compounds useful for therapy and/or prophylaxis in a mammal, and in particular to compounds that are preferential agonists of the Cannabinoid Receptor 2.

The invention relates in particular to a compound of formula (I)

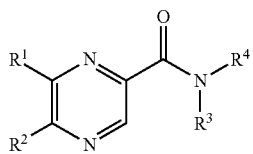

wherein
$R^1$ is cycloalkylalkoxy or haloalkoxy;
$R^2$ is cycloalkyl or haloazetidinyl;
$R^3$ and $R^4$ are independently selected from alkyl, alkoxy, alkoxyalkyl and alkoxycarbonylalkyl;
or $R^3$ and $R^4$ together with the nitrogen atom to which they are attached form heterocyclyl or substituted heterocyclyl, wherein heterocyclyl is pyrrolidinyl, morpholinyl, oxomorpholinyl, 2-oxo-5-aza-bicyclo[2.2.1]heptyl, 7-oxa-4-aza-spiro[2.5]octyl, piperazinyl, 2-oxa-6-aza-spiro[3.4]octyl, piperidinyl, thiomorpholinyl or 5-azaspiro[2.4]heptyl, and wherein substituted heterocyclyl is heterocyclyl substituted with one to four substituents independently selected from alkyl, halogen, aminocarbonyl, hydroxyalkyl, alkoxycarbonyl, alkylthiocarbamoyl, alkylcarbonyloxy and hydroxyl;
or a pharmaceutically acceptable salt or ester thereof.

The compound of formula (I) is particularly useful in the treatment or prophylaxis of e.g. pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis.

The compound of formula (I) is in particular useful in the treatment or prophylaxis of diabetic retinopathy, retinal vein occlusion or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in preconditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. Particular examples of alkyl are methyl, ethyl, isopropyl, butyl and tert.-butyl, in particular methyl, ethyl and tert.-butyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. A particular example of "cycloalkyl" is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy. Particular "alkoxy" are methoxy and ethoxy, and in particular methoxy.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. A particular "halogen" is fluorine.

The term "haloalkyl", alone or in combination, denotes an alkyl group substituted with at least one halogen, particularly substituted with one to five halogens, particularly one to three halogens. A particular "haloalkyl" is trifluoroethyl.

The term "haloalkoxy", alone or in combination, denotes an alkoxy group substituted with at least one halogen, particularly substituted with one to five halogens, particularly one to three halogens. Particular "haloalkoxy" are trifluoroethoxy, fluoroethoxy, fluoropropyloxy, difluoroethoxy and difluoropropyloxy. A particular "haloalkoxy" is trifluoroethoxy.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—NH$_2$), the secondary amino group (—NH—), or the tertiary amino group (—N—).

The term "aminocarbonyl", alone or in combination, signifies the —C(O)—NH$_2$ group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to a compound of formula (I) wherein $R^3$ and $R^4$ are independently selected from alkyl, alkoxy, alkoxyalkyl and alkoxycarbonylalkyl;

or $R^3$ and $R^4$ together with the nitrogen atom to which they are attached form heterocyclyl or substituted heterocyclyl, wherein heterocyclyl is pyrrolidinyl, morpholinyl, oxomorpholinyl, 2-oxo-5-aza-bicyclo[2.2.1]heptyl, 7-oxa-4-aza-spiro[2.5]octyl, piperazinyl, 2-oxa-6-aza-spiro[3.4]octyl, piperidinyl or thiomorpholinyl, and wherein substituted heterocyclyl is heterocyclyl substituted with one to four substituents independently selected from alkyl, halogen, aminocarbonyl, hydroxyalkyl, alkoxycarbonyl, alkylthiocarbamoyl and alkylcarbonyloxy.

The invention relates in particular to:

A compound of formula (I) wherein $R^1$ is cycloalkylalkoxy;

A compound of formula (I) wherein $R^1$ is cyclopropylmethoxy or trifluoroethoxy;

A compound of formula (I) wherein $R^1$ is cyclopropylmethoxy;

A compound of formula (I) wherein $R^2$ is cyclopropyl or difluoroazetidinyl;

A compound of formula (I) wherein $R^3$ and $R^4$ are independently selected from alkyl, alkoxy, alkoxyalkyl and alkoxycarbonylalkyl, or wherein $R^3$ and $R^4$ together with the nitrogen atom to which they are attached form substituted pyrrolidinyl, substituted morpholinyl, substituted oxomorpholinyl, substituted piperidinyl, substituted thiomorpholinyl or substituted 5-azaspiro[2.4]heptyl, wherein substituted pyrrolidinyl, substituted morpholinyl, substituted oxomorpholinyl, substituted piperidinyl, substituted thiomorpholinyl or substituted 5-azaspiro[2.4]heptyl are pyrrolidinyl, morpholinyl, oxomorpholinyl, piperidiny, thiomorpholinyl or 5-azaspiro[2.4]heptyl substituted with one to four substituents independently selected from alkyl, halogen, aminocarbonyl, hydroxyalkyl, alkoxycarbonyl, alkylthiocarbamoyl, alkylcarbonyloxy and hydroxyl, or wherein $R^3$ and $R^4$ together with the nitrogen atom to which they are attached form 2-oxo-5-aza-bicyclo[2.2.1]heptyl, 7-oxa-4-aza-spiro[2.5]octyl, piperazinyl or 2-oxa-6-aza-spiro[3.4]octyl;

A compound of formula (I) wherein $R^3$ and $R^4$ are independently selected from alkyl, alkoxy, alkoxyalkyl and alkoxycarbonylalkyl, or wherein $R^3$ and $R^4$ together with the nitrogen atom to which they are attached form substituted pyrrolidinyl, substituted morpholinyl, substituted oxomorpholinyl, substituted piperidinyl or substituted thiomorpholinyl, wherein substituted pyrrolidinyl, substituted morpholinyl, substituted oxomorpholinyl, substituted piperidinyl or substituted thiomorpholinyl are pyrrolidinyl, morpholinyl, oxomorpholinyl, piperidinyl or thiomorpholinyl substituted with one to four substituents independently selected from alkyl, halogen, aminocarbonyl, hydroxyalkyl, alkoxycarbonyl, alkylthiocarbamoyl and alkylcarbonyloxy, or wherein $R^3$ and $R^4$ together with the nitrogen atom to which they are attached form 2-oxo-5-aza-bicyclo[2.2.1]heptyl, 7-oxa-4-aza-spiro[2.5]octyl, piperazinyl or 2-oxa-6-aza-spiro[3.4]octyl;

A compound of formula (I) wherein $R^3$ and $R^4$ are independently selected from alkyl, alkoxy and alkoxyalkyl, or wherein $R^3$ and $R^4$ together with the nitrogen atom to which they are attached form heterocyclyl or substituted heterocyclyl, wherein heterocyclyl is pyrrolidinyl, morpholinyl or 5-azaspiro[2.4]heptyl, and wherein substituted heterocyclyl is heterocyclyl substituted with one to three substituents independently selected from alkyl, halogen and aminocarbonyl;

A compound of formula (I) wherein $R^3$ and $R^4$ are independently selected from methyl, tert.-butyl, methoxyethyl or methoxybutyl, or wherein $R^3$ and $R^4$ together with the nitrogen atom to which they are attached form dimethylmorpholinyl, dimethylpyrrolidinyl, (aminocarbonyl)(difluoro)pyrrolidinyl, (aminocarbonyl)(dimethyl)pyrrolidinyl or (aminocarbonyl)5-azaspiro[2.4]heptyl;

A compound of formula (I) wherein $R^3$ and $R^4$ are independently selected from alkyl, alkoxy and alkoxyalkyl, or wherein $R^3$ and $R^4$ together with the nitrogen atom to which they are attached form heterocyclyl or substituted heterocyclyl, wherein heterocyclyl is pyrrolidinyl or morpholinyl, and wherein substituted heterocyclyl is heterocyclyl substituted with one to three substituents independently selected from alkyl, halogen and aminocarbonyl;

A compound of formula (I) wherein $R^3$ and $R^4$ are independently selected from methyl, tert.-butyl, methoxyethyl or methoxybutyl, or wherein $R^3$ and $R^4$ together with the nitrogen atom to which they are attached form dimethylmorpholinyl, dimethylpyrrolidinyl, (aminocarbonyl)(difluoro)pyrrolidinyl or (aminocarbonyl)(dimethyl)pyrrolidinyl;

A compound of formula (I) wherein $R^3$ and $R^4$ are independently selected from methyl, ethyl, isopropyl, tert.-butyl, methoxyethyl, ethoxycarbonylmethyl and methoxybutyl or wherein $R^3$ and $R^4$ together with the nitrogen atom to which they are attached form methylpyrrolidinyl, dimethylpyrrolidinyl dimethylmorpholinyl, 2-oxo-5-aza-bicyclo[2.2.1]heptyl, difluoropyrrolidinyl, 7-oxa-4-aza-spiro[2.5]octyl, methoxycarbonylpyrrolidinyl, (aminocarbonyl)(difluoro)pyrrolidinyl, hydroxyethylpiperazinyl, oxomorpholinyl, dimethylthiocarbamoylpyrrolidinyl, (methylcarbonyloxy)(methyl)pyrrolidinyl, tetrafluoropyrrolidinyl, methylcarbonyloxy pyrrolidinyl, 2-oxa-6-aza-spiro[3.4]octyl, aminocarbonylpiperidinyl, aminocarbonylthiomorpholinyl, (aminocarbonyl)5-azaspiro[2.4]heptyl or (hydroxy)(alkyl)(aminocarbonyl)pyrrolidinyl; and A compound of formula (I) wherein $R^3$ and $R^4$ are independently selected from methyl, ethyl, isopropyl, tert.-butyl, methoxyethyl, ethoxycarbonylmethyl and methoxybutyl or wherein $R^3$ and $R^4$ together with the nitrogen atom to which they are attached form methylpyrrolidinyl, dimethylpyrrolidinyl dimethylmorpholinyl, 2-oxo-5-aza-bicyclo[2.2.1]heptyl, difluoropyrrolidinyl, 7-oxa-4-aza-spiro[2.5]octyl, methoxycarbonylpyrrolidinyl, (aminocarbonyl)(difluoro)pyrrolidinyl, hydroxyethylpiperazinyl, oxomorpholinyl, dimethylthiocarbamoylpyrrolidinyl, (methylcarbonyloxy)(methyl)pyrrolidinyl, tetrafluoropyrrolidinyl, methylcarbonyloxy pyrrolidinyl, 2-oxa-6-aza-spiro[3.4]octyl, aminocarbonylpiperidinyl or aminocarbonylthiomorpholinyl.

The invention further relates to a compound of formula (I) selected from
(5-Cyclopropyl-6-cyclopropylmethoxy-pyrazin-2-yl)-((R)-2-methyl-pyrrolidin-1-yl)-methanone;
[6-Cyclopropylmethoxy-5-(3,3-difluoro-azetidin-1-yl)-pyrazin-2-yl]-((R)-2-methyl-pyrrolidin-1-yl)-methanone;
6-Cyclopropylmethoxy-5-(3,3-difluoro-azetidin-1-yl)-pyrazine-2-carboxylic acid tert-butyl-(2-methoxy-ethyl)-amide;
[6-Cyclopropylmethoxy-5-(3,3-difluoro-azetidin-1-yl)-pyrazin-2-yl]-(3,3-dimethyl-morpholin-4-yl)-methanone;
[6-Cyclopropylmethoxy-5-(3,3-difluoro-azetidin-1-yl)-pyrazin-2-yl]-((S)-2-methyl-pyrrolidin-1-yl)-methanone;
[6-Cyclopropylmethoxy-5-(3,3-difluoro-azetidin-1-yl)-pyrazin-2-yl]-(1R,4R)-2-oxa-5-aza-bicyclo[2.2.1]hept-5-yl-methanone;
6-Cyclopropylmethoxy-5-(3,3-difluoro-azetidin-1-yl)-pyrazine-2-carboxylic acid tert-butyl-methyl-amide;
[6-Cyclopropylmethoxy-5-(3,3-difluoro-azetidin-1-yl)-pyrazin-2-yl]-(3,3-difluoro-pyrrolidin-1-yl)-methanone;
6-Cyclopropylmethoxy-5-(3,3-difluoro-azetidin-1-yl)-pyrazine-2-carboxylic acid ethyl-isopropyl-amide;
[6-Cyclopropylmethoxy-5-(3,3-difluoro-azetidin-1-yl)-pyrazin-2-yl]-(7-oxa-4-aza-spiro[2.5]oct-4-yl)-methanone;
{tert-Butyl-[6-cyclopropylmethoxy-5-(3,3-difluoro-azetidin-1-yl)-pyrazine-2-carbonyl]-amino}-acetic acid ethyl ester;
6-Cyclopropylmethoxy-5-(3,3-difluoro-azetidin-1-yl)-pyrazine-2-carboxylic acid (2-methoxy-1,1-dimethyl-ethyl)-methyl-amide;
[6-Cyclopropylmethoxy-5-(3,3-difluoro-azetidin-1-yl)-pyrazin-2-yl]-(2,2-dimethyl-morpholin-4-yl)-methanone;
5-Cyclopropyl-6-cyclopropylmethoxy-pyrazine-2-carboxylic acid (2-methoxy-1,1-dimethyl-ethyl)-methyl-amide;
(5-Cyclopropyl-6-cyclopropylmethoxy-pyrazin-2-yl)-(2,2-dimethyl-pyrrolidin-1-yl)-methanone;
(S)-1-(5-Cyclopropyl-6-cyclopropylmethoxy-pyrazine-2-carbonyl)-pyrrolidine-2-carboxylic acid methyl ester;
(5-Cyclopropyl-6-cyclopropylmethoxy-pyrazin-2-yl)-(7-oxa-4-aza-spiro[2.5]oct-4-yl)-methanone;
(S)-1-(5-Cyclopropyl-6-cyclopropylmethoxy-pyrazine-2-carbonyl)-4,4-difluoro-pyrrolidine-2-carboxylic acid amide;
(S)-1-[6-Cyclopropylmethoxy-5-(3,3-difluoro-azetidin-1-yl)-pyrazine-2-carbonyl]-4,4-difluoro-pyrrolidine-2-carboxylic acid amide;
[6-Cyclopropylmethoxy-5-(3,3-difluoro-azetidin-1-yl)-pyrazin-2-yl]-[4-(2-hydroxy-ethyl)-piperazin-1-yl]-methanone;
[6-Cyclopropylmethoxy-5-(3,3-difluoro-azetidin-1-yl)-pyrazin-2-yl]-(2,2-dimethyl-pyrrolidin-1-yl)-methanone;
(R)-1-[6-Cyclopropylmethoxy-5-(3,3-difluoro-azetidin-1-yl)-pyrazine-2-carbonyl]-pyrrolidine-2-carboxylic acid methyl ester;
4-[6-Cyclopropylmethoxy-5-(3,3-difluoro-azetidin-1-yl)-pyrazine-2-carbonyl]-morpholin-2-one;
(R)-1-[6-Cyclopropylmethoxy-5-(3,3-difluoro-azetidin-1-yl)-pyrazine-2-carbonyl]-pyrrolidine-2-carbothioic acid dimethylamide;
Acetic acid 1-(5-cyclopropyl-6-cyclopropylmethoxy-pyrazine-2-carbonyl)-3-methyl-pyrrolidin-3-yl ester;
(5-Cyclopropyl-6-cyclopropylmethoxy-pyrazin-2-yl)-(3,3,4,4-tetrafluoro-pyrrolidin-1-yl)-methanone;
Acetic acid (S)-1-[6-cyclopropylmethoxy-5-(3,3-difluoro-azetidin-1-yl)-pyrazine-2-carbonyl]-pyrrolidin-3-yl ester;
[6-Cyclopropylmethoxy-5-(3,3-difluoro-azetidin-1-yl)-pyrazin-2-yl]-(2-oxa-6-aza-spiro[3.4]oct-6-yl)-methanone;
Acetic acid 1-[6-cyclopropylmethoxy-5-(3,3-difluoro-azetidin-1-yl)-pyrazine-2-carbonyl]-3-methyl-pyrrolidin-3-yl ester;
[6-Cyclopropylmethoxy-5-(3,3-difluoro-azetidin-1-yl)-pyrazin-2-yl]-(3,3,4,4-tetrafluoro-pyrrolidin-1-yl)-methanone;
5-(3,3-Difluoro-azetidin-1-yl)-6-(2,2,2-trifluoro-ethoxy)-pyrazine-2-carboxylic acid tert-butyl-methyl-amide;
[5-(3,3-Difluoro-azetidin-1-yl)-6-(2,2,2-trifluoro-ethoxy)-pyrazin-2-yl]-(2,2-dimethyl-pyrrolidin-1-yl)-methanone;
1-[6-Cyclopropylmethoxy-5-(3,3-difluoro-azetidin-1-yl)-pyrazine-2-carbonyl]-piperidine-2-carboxylic acid amide;
1-(5-Cyclopropyl-6-cyclopropylmethoxy-pyrazine-2-carbonyl)-4,4-dimethyl-pyrrolidine-2-carboxylic acid amide;
1-[6-Cyclopropylmethoxy-5-(3,3-difluoro-azetidin-1-yl)-pyrazine-2-carbonyl]-4,4-dimethyl-pyrrolidine-2-carboxylic acid amide;
(−)-1-[6-Cyclopropylmethoxy-5-(3,3-difluoro-azetidin-1-yl)-pyrazine-2-carbonyl]-piperidine-2-carboxylic acid amide;
(−)-4-[6-Cyclopropylmethoxy-5-(3,3-difluoro-azetidin-1-yl)-pyrazine-2-carbonyl]-thiomorpholine-3-carboxylic acid amide;
(−)-1-[6-Cyclopropylmethoxy-5-(3,3-difluoro-azetidin-1-yl)-pyrazine-2-carbonyl]-4,4-dimethyl-pyrrolidine-2-carboxylic acid amide; and
(−)-1-(5-Cyclopropyl-6-cyclopropylmethoxy-pyrazine-2-carbonyl)-4,4-dimethyl-pyrrolidine-2-carboxylic acid amide.

The invention further relates to a compound of formula (I) selected from
(±)-5-[6-(Cyclopropylmethoxy)-5-(3,3-difluoroazetidin-1-yl)pyrazine-2-carbonyl]-5-azaspiro[2.4]heptane-6-carboxamide;
(2S)-1-[6-(Cyclopropylmethoxy)-5-(3,3-difluoroazetidin-1-yl)pyrazine-2-carbonyl]-4-hydroxy-4-methylpyrrolidine-2-carboxamide; and
(2S)-1-[5-(3,3-Difluoroazetidin-1-yl)-6-(2,2-difluoroethoxy)pyrazine-2-carbonyl]-4,4-difluoro-pyrrolidine-2-carboxamide.

The invention further relates to a compound of formula (I) selected from
6-Cyclopropylmethoxy-5-(3,3-difluoro-azetidin-1-yl)-pyrazine-2-carboxylic acid tert-butyl-(2-methoxy-ethyl)-amide;
[6-Cyclopropylmethoxy-5-(3,3-difluoro-azetidin-1-yl)-pyrazin-2-yl]-(3,3-dimethyl-morpholin-4-yl)-methanone;
6-Cyclopropylmethoxy-5-(3,3-difluoro-azetidin-1-yl)-pyrazine-2-carboxylic acid tert-butyl-methyl-amide;
6-Cyclopropylmethoxy-5-(3,3-difluoro-azetidin-1-yl)-pyrazine-2-carboxylic acid (2-methoxy-1,1-dimethyl-ethyl)-methyl-amide;
(5-Cyclopropyl-6-cyclopropylmethoxy-pyrazin-2-yl)-(2,2-dimethyl-pyrrolidin-1-yl)-methanone;
(S)-1-[6-Cyclopropylmethoxy-5-(3,3-difluoro-azetidin-1-yl)-pyrazine-2-carbonyl]-4,4-difluoro-pyrrolidine-2-carboxylic acid amide;
[6-Cyclopropylmethoxy-5-(3,3-difluoro-azetidin-1-yl)-pyrazin-2-yl]-(2,2-dimethyl-pyrrolidin-1-yl)-methanone;

1-(5-Cyclopropyl-6-cyclopropylmethoxy-pyrazine-2-carbonyl)-4,4-dimethyl-pyrrolidine-2-carboxylic acid amide; and (−)-1-[6-Cyclopropylmethoxy-5-(3,3-difluoro-azetidin-1-yl)-pyrazine-2-carbonyl]-4,4-dimethyl-pyrrolidine-2-carboxylic acid amide.

The invention further relates to the compound (±)-5-[6-(cyclopropylmethoxy)-5-(3,3-difluoroazetidin-1-yl)pyrazine-2-carbonyl]-5-azaspiro[2.4]heptane-6-carboxamide.

The compound of formula (I) can be prepared by a process, which process comprises coupling a compound of formula II

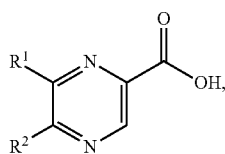

wherein $R^1$ an $R^2$ are as defined herein before, with an amine of the formula III

wherein $R^3$ and $R^4$ are as defined herein before, by amide coupling methods known in the art, as for example with the help of an amide coupling agent under basic conditions, and, if desired, converting the resulting compound of formula (I) into a pharmaceutically acceptable salt thereof.

Unless otherwise indicated, $R^1$ to $R^4$ have in the following schemes the significance given above.

Compounds of formula III or II may contain functional groups that would interfere with the coupling procedures described for the amide coupling step (II to I). In this case it is understood that III or II need to be suitably protected by methods known in the art before conducting the amide coupling procedure and compounds need to be deprotected after the coupling step by methods known in the art to deliver compounds of formula (I).

Amide coupling agents for the reaction of compounds of formula II with amines of formula III are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), or O-benzotriazole-N,N,N',N'-tetramethyl-uronium-hexafluoro-phosphate (HBTU). Particular coupling agents are TBTU and HATU. Suitable bases include triethylamine, N-methylmorpholine and particularly diisopropylethylamine. Alternative methods known in the art may commence by preparing the acid chloride from II and coupling with an amine of formula III in the presence of a suitable base.

The synthesis of the compound of formula (I) can, for example, be accomplished according to the following schemes.

Following the procedure according to scheme 1, compound AA (5-chloro-pyrazine-2-carboxylic acid methyl ester, CAN 33332-25-1) can be used as starting material for the synthesis of compounds I-a where $R^2$ is haloazetidinyl ($R^{2a}$ is haloazetidinyl). AA is either commercially available, or can be synthesized by a person skilled in the art as described in the literature.

Compound AB can be prepared from AA by reacting with the corresponding haloazetidine in the presence of a base, particularly triethylamine, in an inert solvent, particularly dioxane at temperatures ranging from room temperature to 45° C.

Conversion of compound AB to AC can be achieved by electrophilic aromatic bromination in a suitable solvent, particularly by bromination with N-bromosuccinimide in chloroform at elevated temperature, particularly at 60° C., or by using other conditions known in the literature.

The saponification of the ester of general formula AC by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to the acid of general formula AD.

Scheme 1

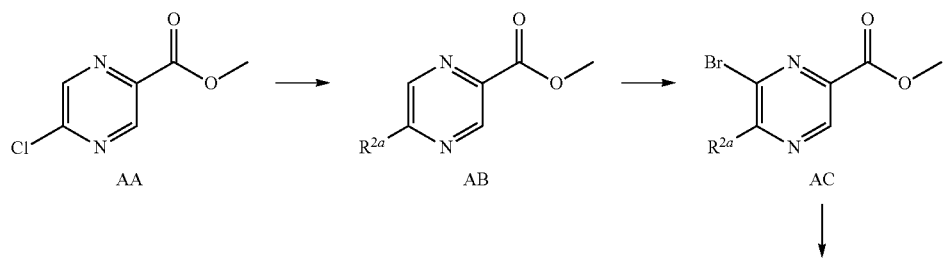

-continued

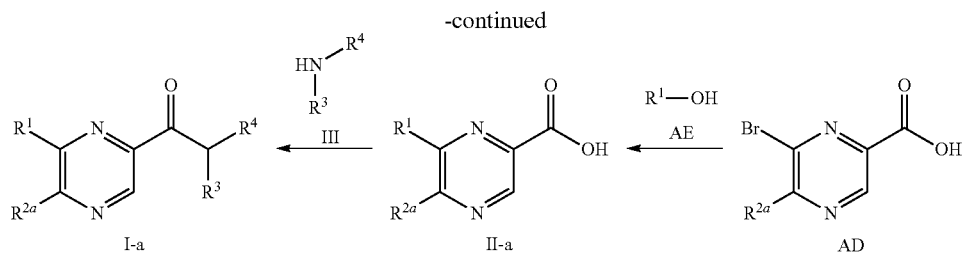

Compounds AD can be transformed to compounds II-a by reaction with a suitably substituted primary or secondary alcohol AE in the presence of a base, for example potassium hydroxide, with or without an inert solvent, for example DMSO, at temperatures ranging from room temperature to the reflux temperature of the solvent, particularly at room temperature.

Compound II-a can be further elaborated to compound I-a by coupling a compound of formula II-a with an amine of the formula III by amide coupling methods known in the art, as for example with the help of an amide coupling agent under basic conditions. For example coupling reagents like N,N'-carbonyl-diimidazole (CDI), N,N'-dicyclohexylcarbo-diimide (DCC), 1-(3-dimethylaminopropyl)-3-ethylcarbodi-imide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriaz-ole (HOBT), O-benzotriazol-1-yl-N,N,N',N'-tetramethyl-uronium tetrafluoroborate (TBTU), and O-benzotriazole-N,N,N',N'-tetramethyl-uronium-hexafluoro-phosphate (HBTU) can be employed to affect such transformation. A convenient method is to use for example 0-benzotriazole-N,N,N',N'-tetramethyl-uronium-hexafluoro-phosphate (HBTU) and a base, for example N-ethyl-N-isopropylpro-pan-2-amine (DIEA) in an inert solvent such as for example dimethylformamide at room temperature. Alternative methods known in the art may commence by preparing the acid chloride from II-a, and coupling with an amine of formula III in the presence of a suitable base.

Amines III are either commercially available, described in the literature, can be synthesized by a person skilled in the art or obtained as described in the experimental part.

If one of the starting materials, compounds of formulae AE or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae AE or III contain chiral centers, pyridines of formula I-a can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbens or a chiral eluent.

Following the procedure according to scheme 2, compound BA (3,5-dibromo-2-pyrazinamine, CAN 24241-18-7) can be used as starting material for the synthesis of compounds I-b where $R^2$ is cycloalkyl ($R^{2b}$ is cycloalkyl).

Compound BA can be transformed to compounds BB by reaction with a suitably substituted primary or secondary alcohol AE in the presence of a base, for example sodium hydride, with or without an inert solvent, for example DMF, at temperatures ranging from room temperature to the reflux temperature of the solvent, particularly at room temperature.

The Boc-protection of compounds of general formula BB by methods well known to the ones skilled in the art—using e.g. di-tert-butyl dicarbonate in an inert solvent, particularly dichloromethane in the presence of a catalytic amount of base, particularly dimethylaminopyridine—leads to compounds of general formula BC if an excess of di-tert-butyl dicarbonate is employed in the reaction.

Scheme 2

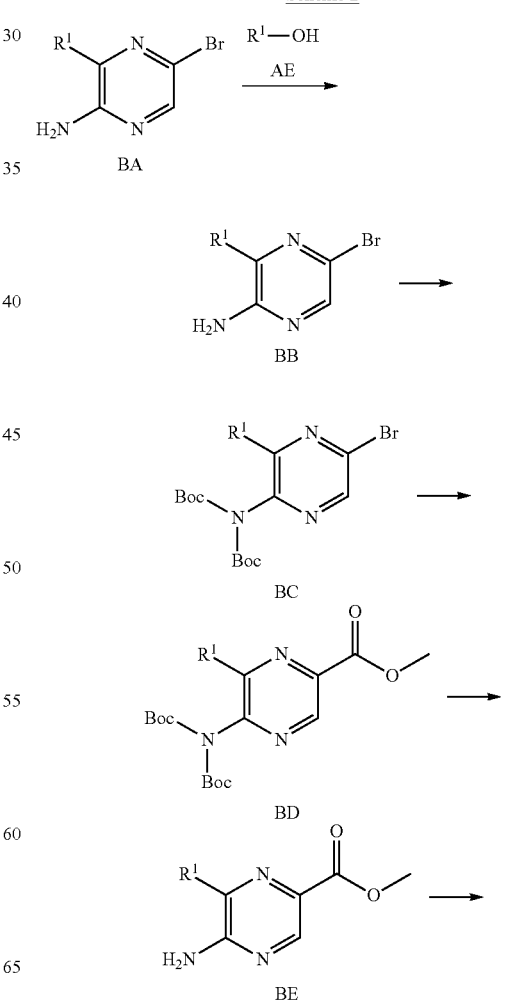

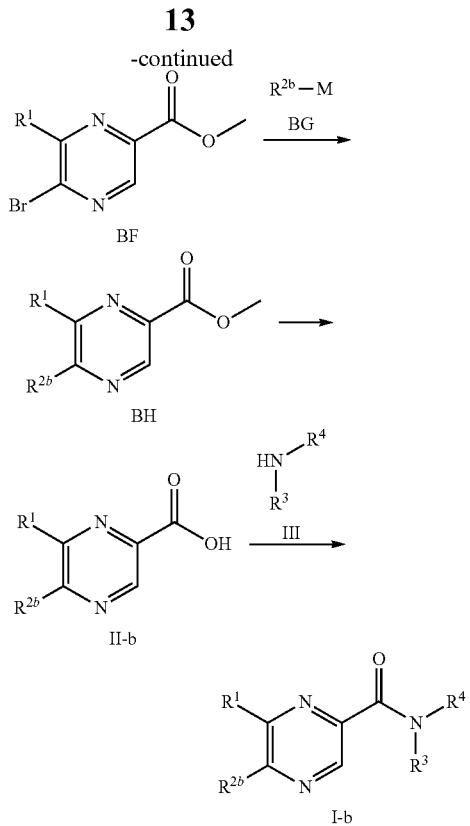

Compounds of the general formula BD can be obtained from compounds of the general formula BC by palladium (II), particularly palladium(II) acetate catalyzed carbonylation in the presence of a suitable base such as a tertiary amine base, particularly triethylamine in a suitable solvent such as an alcohol, particularly methanol.

The solvolysis of boc-protected compounds of general formula BD by methods well known to the ones skilled in the art—using e.g. a protic solvent, particularly methanol at elevated temperatures, particularly reflux temperature—leads to compounds of general formula BE.

Compounds of the general formula BF can be obtained from compounds of the general formula BE by reaction with nitrosating agents such as a metal nitrite or an organic nitrite more particularly tert-butyl nitrite, in the presence of a bromide source such as hydrobromic acid or more particularly trimethylbromosilane in a suitable solvent such as halogenated hydrocarbons more particularly dibromomethane.

Compounds BH where $R^2$ is cycloalkyl ($R^{2b}$ is cycloalkyl) can be prepared from BF by coupling a suitably substituted cycloalkyl or cycloakenyl metal species BG particularly a cyclopropylboronic acid or cyclopropyltrifluoro-borate salt with BF in the presence of a suitable catalyst, particularly a palladium catalyst like palladium(II) acetate in the presence of cyclohexylphosphine in an inert solvent such as toluene at room temperature up to the reflux temperature of the solvent in the presence of a suitable base, like potassium phosphate. In cases where the practitioner skilled in the art chooses to couple with a cycloakenyl metal species, like cycloalkenylboronic acid esters, compounds BH will be obtained only after an additional hydrogenation step, for example by hydrogenation with hydrogen gas in the presence of a palladium catalyst, for example palladium on charcoal, in an inert solvent, for example ethanol, at suitable temperatures and pressures, particularly at ambient temperature and pressure.

The saponification of the ester of general formula BH by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to the acid of general formula II-b.

Compound II-b can be further elaborated to compound I-b by coupling a compound of formula II-b with an amine of the formula III by amide coupling methods known in the art, as for example with the help of an amide coupling agent under basic conditions. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example O-benzotriazole-N,N,N',N'-tetramethyl-uronium-hexafluoro-phosphate (HBTU) and a base, for example N-ethyl-N-isopropylpropan-2-amine (DIEA) in an inert solvent such as for example dimethylformamide at room temperature. Alternative methods known in the art may commence by preparing the acid chloride from II-b and coupling with an amine of formula III in the presence of a suitable base.

Amines III are either commercially available, described in the literature, can be synthesized by a person skilled in the art or obtained as described in the experimental part.

If one of the starting materials, compounds of formulae AE, BG or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae AE, BG or III contain chiral centers, pyridines of formula I-b can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbens or a chiral eluent.

The invention also relates to a process for the preparation of a compound of formula (I) comprising the reaction of a compound of formula (II)

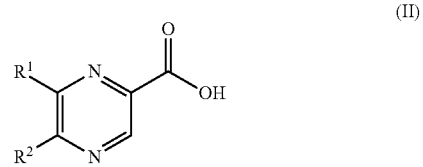

(II)

in the presence of $NHR^3R^4$, an amide coupling agent and a base, wherein $R^1$ to $R^4$ are as defined above.

Suitable amide coupling agents and bases for the process of the invention are as defined above.

The invention also relates in particular to:

The use of a compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis;

A compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis; and A method for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention further particularly relates to a compound of formula (I) for the treatment or prophylaxis of diabetic retinopathy, retinal vein occlusion or uveitis.

The invention is further directed to a compound of formula (I), when manufactured according to a process according to the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. The compounds of the invention may be administered in particular by intravitreal administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations bp=boiling point; CAN=CAS Registry Number; DBU=1,8-diazabicyclo[5.4.0]undec-7-ene; DCM=dichloromethane; DIEA=N-ethyl-N-isopropylpropan-2-amine; DMF=dimethylformamide; DMSO=dimethyl sulfoxide; dppf=1,1'-bis(diphenylphosphino)ferrocene; EI=electron ionization; ESI=electrospray; h=hour; HATU=2-(3H-[1,2,3]triazolo[4,5-b]pyridin-3-yl)-1,1,3,3-tetramethylisouronium hexafluorophosphate(V); HBTU=O-benzotriazole-N,N,N',N'-tetramethyl-uronium-hexafluoro-phosphate; HPLC=LC=high performance liquid chromatography; m-CPBA=meta-chloroperoxybenzoic acid; mp=melting point; MS=mass spectrometry; NMR data are reported in parts per million (δ) relative to internal tetramethylsilane and are referenced to the deuterium lock signal from the sample solvent ($d_6$-DMSO unless otherwise stated); coupling constants (J) are in Hertz; Rt=retention time; TBME=methyl tert-butylether, TBTU=O-(benzotriazol-1-yl)-N,N,N',N'-tetramethyl-uronium-tetrafluoroborate; TEMPO=2,2,6,6-tetra-methylpiperidine 1-oxyl radical; TFA=trifluoroacetic acid; THF=tetrahydrofuran; tlc=thin layer chromatography.

Example 1

(5-Cyclopropyl-6-cyclopropylmethoxy-pyrazin-2-yl)-((R)-2-methyl-pyrrolidin-1-yl)-methanone a) 5-Bromo-3-cyclopropylmethoxy-pyrazin-2-ylamine

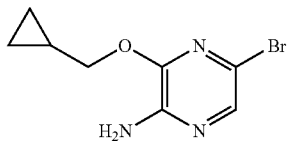 [SMILES: Nc1ncc(Br)nc1OCC1CC1]

To a solution of cyclopropyl-methanol (16.47 mL, 205.62 mmol) in DMSO (200 mL) was added sodium hydride (60% in oil, 4.93 g, 205.62 mmol) at 0° C. and the reaction mixture was stirred at 0° C. for 2 hours. To this suspension was added 3,5-dibromo-pyrazin-2-ylamine (20 g, 79.09 mmol) in DMSO (40 mL) and the mixture was stirred at ambient temperature for 12 hours. The mixture was partitioned between water (300 mL) and ethyl acetate and the organic phase was dried with $Na_2SO_4$, filtered and concentrated in vacuo. The crude material was purified by chromatography (silica gel, 500 g, 10% ethyl acetate in hexane) to give the desired product (14 g, 72.52%) as yellow solid; LC-MS (UV peak area, ESI) 94.7%, 244.0 [MH]$^+$.

b) Di-tert-butyl[5-bromo-3-(cyclopropylmethoxy)pyrazin-2-yl]imidodicarbonate

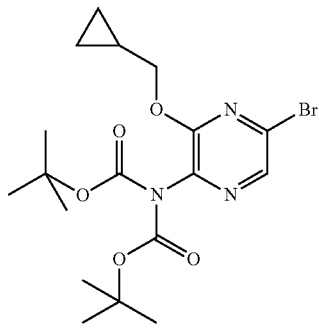 [SMILES: CC(C)(C)OC(=O)N(C(=O)OC(C)(C)C)c1ncc(Br)nc1OCC1CC1]

To a solution of 5-bromo-3-cyclopropylmethoxy-pyrazin-2-ylamine (30 g, 122.91 mmol) in DCM (200 mL) were added di-tert-butyl dicarbonate (67.7 mL, 307.26 mmol) and 4-dimethylaminopyridine (1.49 g, 12.29 mmol). The reaction mixture was stirred at ambient temperature for 18 hours. The mixture was partitioned between water (300 mL) and dichloromethane and the organic phase was separated, washed with brine, dried with $Na_2SO_4$, filtered and concentrated in vacuo. The crude material was purified by chromatography (silica gel, 600 g, 5%-7% ethyl acetate in hexane) to give the desired product (45 g, 82.8%) as yellow oil; LC-MS (UV peak area, ESI) 94.7%, 445.0 [MH]$^+$.

c) Methyl 5-[bis(tert-butoxycarbonyl)amino]-6-(cyclopropylmethoxy)pyrazine-2-carboxylate

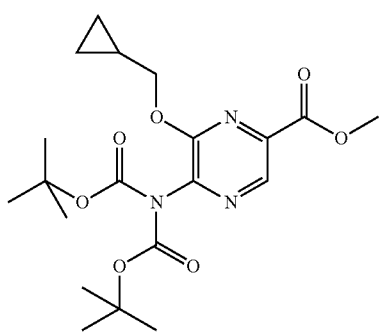 [SMILES: COC(=O)c1cnc(N(C(=O)OC(C)(C)C)C(=O)OC(C)(C)C)c(OCC2CC2)n1]

To a solution of di-tert-butyl[5-bromo-3-(cyclopropylmethoxy)pyrazin-2-yl]imido-dicarbonate (20 g, 45.05 mmol) in methanol (200 mL) was added $PdCl_2.dppf.CH_2Cl_2$ (4.04 g, 4.95 mmol) and triethylamine (9.5 mL, 67.57 mmol) and the mixture was stirred under an atmosphere of 32 bar carbon monoxide at 80° C. for 5 hours. After expansion and cooling, the solid was removed by filtration. The organic phase was separated, washed with brine (300 mL), dried with $Na_2SO_4$, filtered and concentrated in vacuo. The crude material was purified by chromatography (Combi-Flash, 120 g, 15%-20% ethyl acetate in hexane) to give the desired product (14 g, 73.7%) as yellow semi-solid; LC-MS (UV peak area, ESI) 96.1%, 424.4 [MH]$^+$.

d) 5-Amino-6-cyclopropylmethoxy-pyrazine-2-carboxylic acid methyl ester

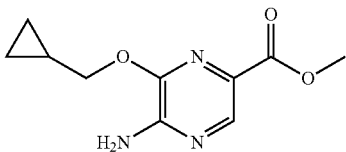 [SMILES: COC(=O)c1cnc(N)c(OCC2CC2)n1]

Methyl 5-[bis(tert-butoxycarbonyl)amino]-6-(cyclopropylmethoxy)pyrazine-2-carboxylate (15 g, 35.46 mmol) was suspended in methanol (150 mL) and water (225 mL) and the mixture was heated at 100° C. for 12 hours. After cooling, a white solid was formed, filtered and dried in vacuo to give the title compound (5.7 g, 72.2%) as off white solid; LC-MS (UV peak area, ESI) 99.7%, 224.2 [MH+].

e) 5-Bromo-6-cyclopropylmethoxy-pyrazine-2-carboxylic acid methyl ester

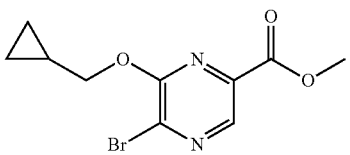 [SMILES: COC(=O)c1cnc(Br)c(OCC2CC2)n1]

5-Amino-6-cyclopropylmethoxy-pyrazine-2-carboxylic acid methyl ester (10 g, 44.84 mmol) was suspended in dibromomethane (150 mL). To this suspension were added trimethylsilyl bromide (14.8 mL, 112.11 mmol) followed by tert-butyl nitrite (57.5 mL, 448.43 mmol) at 0° C. and the mixture was stirred at that temperature for 3 hours. The mixture was partitioned between water (190 mL) and ethyl acetate and the organic phase was washed with brine (200 mL), dried with Na$_2$SO$_4$, filtered and concentrated in vacuo. The crude material was purified by chromatography (Combi-Flash, 80 g, 20% ethyl acetate in hexane) to give the desired product (6.3 g, 46.6%) as white solid; LC-MS (UV peak area, ESI) 90.7%, 287.2 [MH+].

f) 5-Cyclopropyl-6-cyclopropylmethoxy-pyrazine-2-carboxylic acid methyl ester

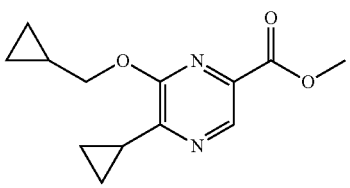 [SMILES: COC(=O)c1cnc(C2CC2)c(OCC2CC2)n1]

5-Bromo-6-cyclopropylmethoxy-pyrazine-2-carboxylic acid methyl ester (5 g, 17.42 mmol), potassium phosphate tribasic (12.9 g, 60.98 mmol) and palladium(II)acetate (389 mg, 1.74 μmol) were dissolved in toluene (45 mL) and water (5 mL) and the reaction mixture was degassed with argon for 15 minutes. Cyclopropylboronic acid (2.9 g, 34.84 mmol) and tricyclohexylphosphine (0.487 g, 1.74 mmol) were added and the reaction mixture was stirred at 60° C. for 16 hours. The mixture was partitioned between water and ethyl acetate and the organic phase was washed with brine (100 mL), dried with Na$_2$SO$_4$, filtered and concentrated in vacuo. The crude material was purified by chromatography (Combi-Flash, 80 g, 10%-15% ethyl acetate in hexane) to give the desired product (2.6 g, 60.1%) as white solid; LC-MS (UV peak area, ESI) 98.9%, 249.2 [MH+].

g) 5-Cyclopropyl-6-cyclopropylmethoxy-pyrazine-2-carboxylic acid

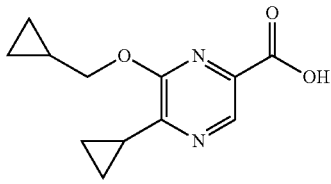 [SMILES: O=C(O)c1cnc(C2CC2)c(OCC2CC2)n1]

To a solution of 5-cyclopropyl-6-cyclopropylmethoxy-pyrazine-2-carboxylic acid methyl ester (7 g, 28.23 mmol) in THF (20 mL) and H$_2$O (10 mL) was added lithium hydroxide (1.54 g, 26.69 mmol) and the mixture was stirred at ambient temperature for 4.5 hours. Solvent was concentrated in vacuo and residue was diluted with H$_2$O (20 mL). The aqueous phase was acidified with hydrochloric acid (1M, pH~2-3) and the solid was separated. The solid was triturated with toluene (25 ml) and dried in vacuo to give the title compound (5.3 g, 86.6%) as white crystalline solid; LC-MS (UV peak area, ESI) 93.2%, 233.2 [M–H⁻].

h) (5-Cyclopropyl-6-cyclopropylmethoxy-pyrazin-2-yl)-((R)-2-methyl-pyrrolidin-1-yl)-methanone

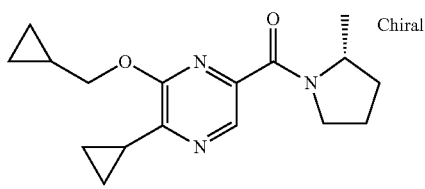 [SMILES: C[C@@H]1CCCN1C(=O)c1cnc(C2CC2)c(OCC2CC2)n1]

5-Cyclopropyl-6-cyclopropylmethoxy-pyrazine-2-carboxylic acid (50 mg, 00.21 mmol) was suspended in DMF (1.5 mL). Mukaiyama Reagent (CAN 878-23-9, 117 mg, 0.42 mmol), DIEA (0.16 mL, 1.12 mmol) and (R)-2-methyl pyrrolidine (CAN 41720-98-3; 15 mg, 0.17 mmol) were added and the reaction mixture was stirred at room temperature for 12 hours. The mixture was extracted with ethyl acetate and water; the organic phase was dried over Na$_2$SO$_4$, filtered and concentrated in vacuo. The crude material was purified by reverse phase preparative HPLC (Xterra-RP18, 10μ, 19×250 mm/acetonitrile/10 mM ammonium acetate in water) to give the desired product (15 mg, 64%) as off white solid; LC-MS (UV peak area, ESI) 90.6%, 302.2 [MH+].

Example 2

[6-Cyclopropylmethoxy-5-(3,3-difluoro-azetidin-1-yl)-pyrazin-2-yl]-((R)-2-methyl-pyrrolidin-1-yl)-methanone a) 5-(3,3-Difluoro-azetidin-1-yl)-pyrazine-2-carboxylic acid methyl ester

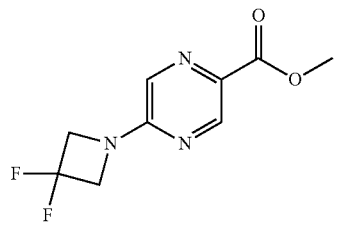 [SMILES: COC(=O)c1cnc(N2CC(F)(F)C2)cn1]

5-Chloro-pyrazine-2-carboxylic acid methyl ester (CAN 33332-25-1; 15 g, 86.92 mmol) was dissolved in dioxane (100 mL). To this solution was added 3,3-difluoroazetidine hydrochloride (CAN 288315-03-7; 13.51 g, 104.31 mmol), and triethyl amine (31.3 mL, 226 mmol). The mixture was stirred 22 hours at 45° C. and afterwards cooled to room temperature. Brine (100 mL) was added and the mixture was extracted with ethyl acetate. The organic phases were washed successively with sodium bicarbonate solution (10%, 300 mL) and brine (200 mL); dried with Na$_2$SO$_4$, filtered and concentrated in vacuo. The crude material was purified by flash chromatography (silica gel, 200 g, 30% to 50% ethyl acetate in hexane) to give the desired product (15 g, 75.3%) as white solid; LC-MS (UV peak area, ESI) 98.6%, 230.4 [MH$^+$].

b) 6-Bromo-5-(3,3-difluoro-azetidin-1-yl)-pyrazine-2-carboxylic acid methyl ester

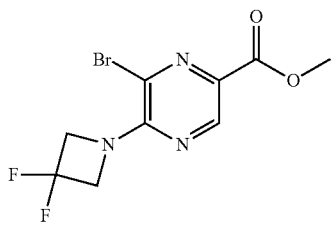 [SMILES: COC(=O)c1cnc(N2CC(F)(F)C2)c(Br)n1]

To a solution of 5-(3,3-difluoro-azetidin-1-yl)-pyrazine-2-carboxylic acid methyl ester (16.5 g, 72.05 mmol) in chloroform (200 mL) was added N-bromosuccinimide (25.64 g, 151.34 mmol) portion wise at 60° C. and the mixture was stirred at 60° C. for 20 hours. After cooling, water (400 mL) was added and the organic phase was separated, the organic phase was washed successively with water (200 mL), brine (200 mL); dried with Na$_2$SO$_4$, filtered and concentrated in vacuo. The crude material was purified by flash chromatography (silica gel, 200 g, 50% ethyl acetate in hexane) to give the desired product (17 g, 77.2%) as light yellow solid; LC-MS (UV peak area, ESI) 97.8%, 308.0 [MH$^+$].

c) 6-Bromo-5-(3,3-difluoro-azetidin-1-yl)-pyrazine-2-carboxylic acid

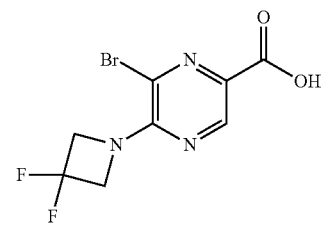 [SMILES: O=C(O)c1cnc(N2CC(F)(F)C2)c(Br)n1]

To a solution of 6-bromo-5-(3,3-difluoro-azetidin-1-yl)-pyrazine-2-carboxylic acid methyl ester (6.0 g, 19.48 mmol) in THF (20 mL) and H$_2$O (10 mL) was added lithium hydroxide (1.06 g, 25.32 mmol) and the mixture was stirred at ambient temperature for 5 hours. Solvent was concentrated in vacuo and residue was diluted with H$_2$O (30 mL). The aqueous phase was acidified with hydrochloric acid (1M, pH~2-3) and the solid was separated. The solid was triturated with toluene (25 mL) and dried in vacuo to give the title compound (4.0 g, 70.2%) as white crystalline solid; LC-MS (UV peak area, ESI) 100%, 294.2 [MH$^+$].

d) 6-Cyclopropylmethoxy-5-(3,3-difluoro-azetidin-1-yl)-pyrazine-2-carboxylic acid

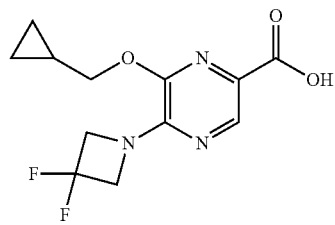 [SMILES: O=C(O)c1cnc(N2CC(F)(F)C2)c(OCC2CC2)n1]

To a solution of cyclopropyl-methanol (4.96 mL, 61.21 mmol) in dry DMSO (90 mL) was added potassium hydroxide (5.89 g, 107.12 mmol) portion wise at ambient temperature. To this mixture was added a solution of 6-bromo-5-(3,3-difluoro-azetidin-1-yl)-pyrazine-2-carboxylic acid (9.0 g, 30.61 mmol) in DMSO (10 mL). The reaction mixture was stirred at ambient temperature for 3 hours. Water (100 mL) was added and the aqueous was acidified with aqueous hydrochloric acid (10%, pH~3-4), and the solid was filtered. The solid was triturated with toluene (50 mL) and dried in vacuo to give the title compound (8.0 g, 91.6%) as white crystalline solid; LC-MS (UV peak area, ESI) 100%, 286.2 [MH$^+$].

e) [6-Cyclopropylmethoxy-5-(3,3-difluoro-azetidin-1-yl)-pyrazin-2-yl]-((R)-2-methyl-pyrrolidin-1-yl)-methanone

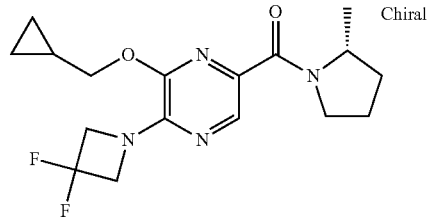 [SMILES: C[C@@H]1CCCN1C(=O)c1cnc(N2CC(F)(F)C2)c(OCC2CC2)n1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and (R)-2-methyl pyrrolidine (CAN 41720-98-3; 15 mg, 0.17 mmol) as starting materials and isolated (25 mg, 40.4%) as off white solid; LC-MS (UV peak area, ESI) 98.42%, 431.0 [MH$^+$].

Example 3

6-Cyclopropylmethoxy-5-(3,3-difluoro-azetidin-1-yl)-pyrazine-2-carboxylic acid tert-butyl-(2-methoxy-ethyl)-amide

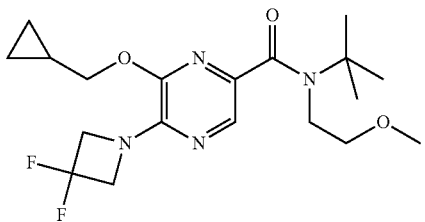 [SMILES: COCCN(C(=O)c1cnc(N2CC(F)(F)C2)c(OCC2CC2)n1)C(C)(C)C]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and tert-butyl-(2-methoxy-ethyl)-amine (CAN 22687-22-5; 20 mg, 0.14 mmol) as starting materials and isolated (35 mg, 69.9%) as off white solid; LC-MS (UV peak area, ESI) 100%, 399.2 [MH$^+$].

Example 4

[6-Cyclopropylmethoxy-5-(3,3-difluoro-azetidin-1-yl)-pyrazin-2-yl]-(3,3-dimethyl-morpholin-4-yl)-methanone

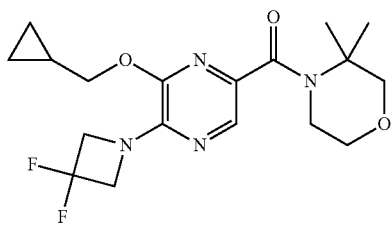 [SMILES: CC1(C)COCCN1C(=O)c1cnc(N2CC(F)(F)C2)c(OCC2CC2)n1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and 3,3-dimethylmorpholine hydrochloride (CAN 59229-63-9; 22 mg, 0.14 mmol) as starting materials and isolated (50 mg, 67.08%) as white solid; LC-MS (UV peak area, ESI) 93.6%, 383.2 [MH]$^+$.

Example 5

[6-Cyclopropylmethoxy-5-(3,3-difluoro-azetidin-1-yl)-pyrazin-2-yl]-((S)-2-methyl-pyrrolidin-1-yl)-methanone

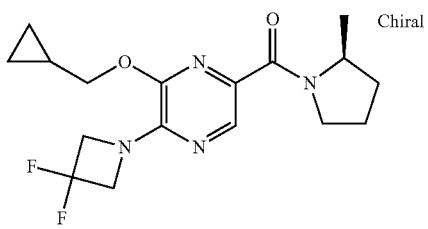 [SMILES: C[C@H]1CCCN1C(=O)c1cnc(N2CC(F)(F)C2)c(OCC2CC2)n1]

The title compound was synthesized in analogy to Example 1h, using 6-cyclopropylmethoxy-5-(3,3-difluoro-azetidin-1-yl)-pyrazine-2-carboxylic acid (Example 2d, 100 mg, 0.35 mmol) and (S)-2-methyl pyrrolidine (CAN 59335-84-1; 25 mg, 0.28 mmol) as starting materials and isolated (74 mg, 59.9%) as white solid; LC-MS (UV peak area, ESI) 99.5%, 353.0 [MH]$^+$.

Example 6

[6-Cyclopropylmethoxy-5-(3,3-difluoro-azetidin-1-yl)-pyrazin-2-yl]-2-oxa-5-aza-bicyclo[2.2.1]hept-5-yl-methanone

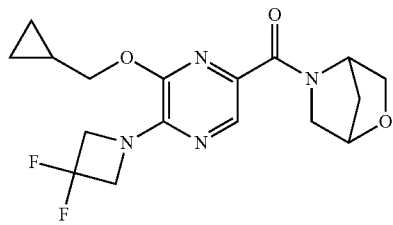 [SMILES: O=C(c1cnc(N2CC(F)(F)C2)c(OCC2CC2)n1)N1CC2CC1CO2]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and 2-oxa-5-aza-bicyclo[2.2.1]heptane (CAN 909186-56-7; 20 mg, 0.17 mmol) as starting materials and isolated (60 mg, 59.9%) as off white solid; LC-MS (UV peak area, ESI) 93.0%, 367.0 [MH$^+$].

Example 7

6-Cyclopropylmethoxy-5-(3,3-difluoro-azetidin-1-yl)-pyrazine-2-carboxylic acid tert-butyl-methyl-amide

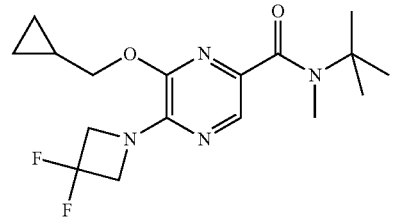 [SMILES: CN(C(=O)c1cnc(N2CC(F)(F)C2)c(OCC2CC2)n1)C(C)(C)C]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and N-tert-butyl-methylamine (CAN 14610-37-8; 25 mg, 0.26 mmol) as starting materials and isolated (46 mg, 74.1%) as off white solid; LC-MS (UV peak area, ESI) 93.8%, 355.2 [MH]$^+$.

Example 8

[6-Cyclopropylmethoxy-5-(3,3-difluoro-azetidin-1-yl)-pyrazin-2-yl]-(3,3-difluoro-pyrrolidin-1-yl)-methanone

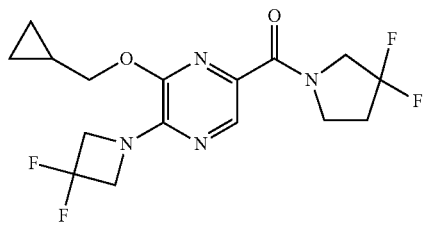 [SMILES: O=C(c1cnc(N2CC(F)(F)C2)c(OCC2CC2)n1)N1CCC(F)(F)C1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and 3,3-difluoro-pyrrolidine hydrochloride (CAN 163457-23-6; 37 mg, 0.26 mmol) as starting materials and isolated (30 mg, 46.1%) as colorless sticky solid; LC-MS (UV peak area, ESI) 99.8%, 375.2 [MH]$^+$.

Example 9

6-Cyclopropylmethoxy-5-(3,3-difluoro-azetidin-1-yl)-pyrazine-2-carboxylic acid ethyl-isopropyl-amide

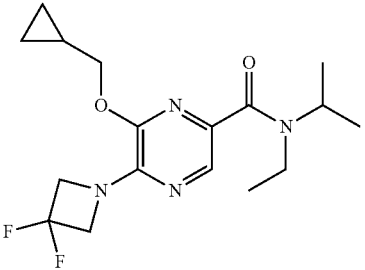 [SMILES: CCN(C(=O)c1cnc(N2CC(F)(F)C2)c(OCC2CC2)n1)C(C)C]

The title compound was synthesized in analogy to Example 1h, using 6-cyclopropylmethoxy-5-(3,3-difluoro-azetidin-1-yl)-pyrazine-2-carboxylic acid (Example 2d, 19.4 mg, 68 µmol) and N-ethyl-2-propanamine (CAN 19961-27-4; 8.2 µL, 68 µmol) as starting materials and isolated (16.8 mg, 70%) as yellow oil; LC-MS (UV peak area, ESI) 99.8%, 375.2 [MH$^+$].

Example 10

[6-Cyclopropylmethoxy-5-(3,3-difluoro-azetidin-1-yl)-pyrazin-2-yl]-(7-oxa-4-aza-spiro[2.5]oct-4-yl)-methanone

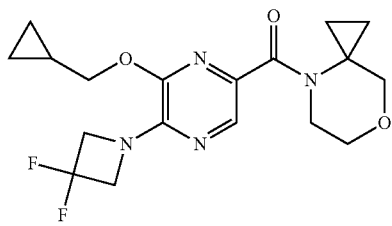 [SMILES: O=C(c1cnc(N2CC(F)(F)C2)c(OCC2CC2)n1)N1CCOCC12CC2]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and 7-oxa-4-azaspiro[2.5]octane (CAN 218595-22-3; 17 mg, 0.14 mmol) as starting materials and isolated (45 mg, 67.4%) as colorless sticky solid; LC-MS (UV peak area, ESI) 100%, 380.8 [MH$^+$].

Example 11

{tert-Butyl-[6-cyclopropylmethoxy-5-(3,3-difluoro-azetidin-1-yl)-pyrazine-2-carbonyl]-amino}-acetic acid ethyl ester

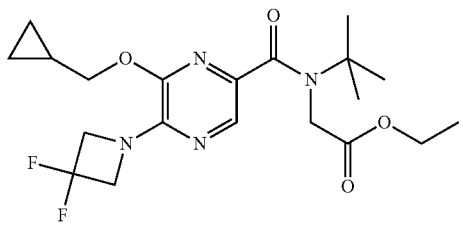 [SMILES: CCOC(=O)CN(C(=O)c1cnc(N2CC(F)(F)C2)c(OCC2CC2)n1)C(C)(C)C]

The title compound was synthesized in analogy to Example 1h, using 6-cyclopropylmethoxy-5-(3,3-difluoro-azetidin-1-yl)-pyrazine-2-carboxylic acid (Example 2d, 100 mg, 0.35 mmol) and tert-butylamino-acetic acid ethyl ester (CAN 37885-76-0; 45 mg, 0.28 mmol) as starting materials and isolated (50 mg, 33.4%) as colorless sticky liquid; LC-MS (UV peak area, ESI) 100%, 427.0 [MH]$^+$.

Example 12

6-Cyclopropylmethoxy-5-(3,3-difluoro-azetidin-1-yl)-pyrazine-2-carboxylic acid (2-methoxy-1,1-dimethyl-ethyl)-methyl-amide

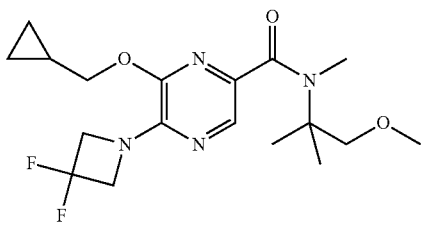 [SMILES: COCC(C)(C)N(C)C(=O)c1cnc(N2CC(F)(F)C2)c(OCC2CC2)n1]

The title compound was synthesized in analogy to Example 1h, using 6-cyclopropylmethoxy-5-(3,3-difluoro-azetidin-1-yl)-pyrazine-2-carboxylic acid (Example 2d, 100 mg, 0.35 mmol) and (2-methoxy-1,1-dimethyl-ethyl)-methyl-amine (CAN 1177316-77-6; 43 mg, 0.28 mmol) as starting materials and isolated (70 mg, 52%) as colorless sticky liquid; LC-MS (UV peak area, ESI) 99.8%, 384.8 [MH]$^+$.

Example 13

[6-Cyclopropylmethoxy-5-(3,3-difluoro-azetidin-1-yl)-pyrazin-2-yl]-(2,2-dimethyl-morpholin-4-yl)-methanone

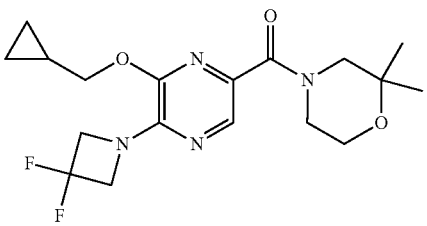 [SMILES: CC1(C)CN(C(=O)c2cnc(N3CC(F)(F)C3)c(OCC3CC3)n2)CCO1]

The title compound was synthesized in analogy to Example 1h, using 6-cyclopropylmethoxy-5-(3,3-difluoro-azetidin-1-yl)-pyrazine-2-carboxylic acid (Example 2d, 100 mg, 0.35 mmol) and 2,2-dimethylmorpholine (CAN 147688-58-2; 33 mg, 0.28 mmol) as starting materials and isolated (60 mg, 44.7%) as white solid; LC-MS (UV peak area, ESI) 100%, 382.8 [MH]$^+$.

Example 14

5-Cyclopropyl-6-cyclopropylmethoxy-pyrazine-2-carboxylic acid (2-methoxy-1,1-dimethyl-ethyl)-methyl-amide

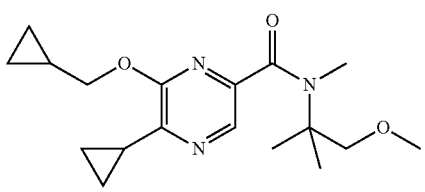 [SMILES: COCC(C)(C)N(C)C(=O)c1cnc(C2CC2)c(OCC2CC2)n1]

The title compound was synthesized in analogy to Example 1h, using 5-cyclopropyl-6-cyclopropylmethoxy-pyrazine-2-carboxylic acid (Example 1g, 50 mg, 0.21 mmol) and (2-methoxy-1,1-dimethyl-ethyl)-methyl-amine (CAN 1177316-77-6; 37.44 mg, 0.32 mmol) as starting materials and isolated (30 mg, 42.1%) as colorless sticky liquid; LC-MS (UV peak area, ESI) 100%, 334.0 [MH]$^+$.

Example 15

(5-Cyclopropyl-6-cyclopropylmethoxy-pyrazin-2-yl)-(2,2-dimethyl-pyrrolidin-1-yl)-methanone

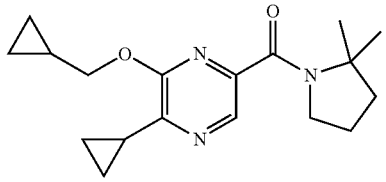 [SMILES: CC1(C)CCCN1C(=O)c1cnc(C2CC2)c(OCC2CC2)n1]

The title compound was synthesized in analogy to Example 1h, using 5-cyclopropyl-6-cyclopropylmethoxy-pyrazine-2-carboxylic acid (Example 1g, 50 mg, 0.21 mmol) and 2,2-dimethylpyrrolidine (CAN 35018-15-6; 51 mg, 0.32 mmol) as starting materials and isolated (65 mg, 97.0%) as colorless sticky liquid; LC-MS (UV peak area, ESI) 100%, 317 [MH$^+$].

Example 16

(S)-1-(5-Cyclopropyl-6-cyclopropylmethoxy-pyrazine-2-carbonyl)-pyrrolidine-2-carboxylic acid methyl ester

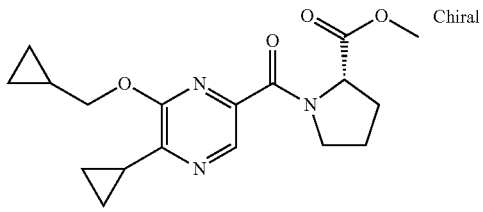 [SMILES: COC(=O)[C@@H]1CCCN1C(=O)c1cnc(C2CC2)c(OCC2CC2)n1]

The title compound was synthesized in analogy to Example 1h, using 5-cyclopropyl-6-cyclopropylmethoxy-pyrazine-2-carboxylic acid (Example 1g, 50 mg, 0.21 mmol) and (S)-pyrrolidine-2-carboxylic acid methyl ester (CAN 43041-12-9; 42 mg, 0.32 mmol) as starting materials and isolated (26 mg, 35.6%) as colorless sticky liquid; LC-MS (UV peak area, ESI) 100%, 345.8 [MH$^+$].

Example 17

(5-Cyclopropyl-6-cyclopropylmethoxy-pyrazin-2-yl)-(7-oxa-4-aza-spiro[2.5]oct-4-yl)-methanone

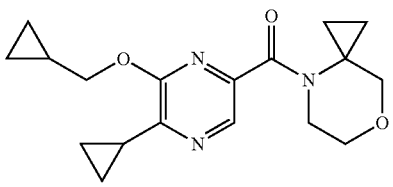 [SMILES: O=C(c1cnc(C2CC2)c(OCC2CC2)n1)N1CCOCC12CC2]

The title compound was synthesized in analogy to Example 1h, using 5-cyclopropyl-6-cyclopropylmethoxy-pyrazine-2-carboxylic acid (Example 1g, 50 mg, 0.21 mmol) and 7-oxa-4-azaspiro[2.5]octane (CAN 126616-59-9; 36.2 mg, 0.32 mmol) as starting materials and isolated (55 mg, 78.5%) as colorless sticky liquid; LC-MS (UV peak area, ESI) 100%, 330.2 [MH$^+$].

Example 18

(S)-1-(5-Cyclopropyl-6-cyclopropylmethoxy-pyrazine-2-carbonyl)-4,4-difluoro-pyrrolidine-2-carboxylic acid amide

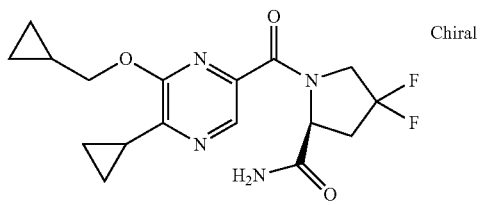 [SMILES: NC(=O)[C@@H]1CC(F)(F)CN1C(=O)c1cnc(C2CC2)c(OCC2CC2)n1]

The title compound was synthesized in analogy to Example 1h, using 5-cyclopropyl-6-cyclopropylmethoxy-pyrazine-2-carboxylic acid (Example 1g, 50 mg, 0.21 mmol) and (2S)-4,4-difluoro-2-pyrrolidinecarboxamide hydrochloride (1:1) (CAN 426844-51-1; 43.8 mg, 0.24 mmol) as starting materials and isolated (62 mg, 79%) as light yellow solid; LC-MS (UV peak area, ESI) 100%, 411.1486 [M+HCOO$^+$].

Example 19

(S)-1-[6-Cyclopropylmethoxy-5-(3,3-difluoro-azetidin-1-yl)-pyrazine-2-carbonyl]-4,4-difluoro-pyrrolidine-2-carboxylic acid amide

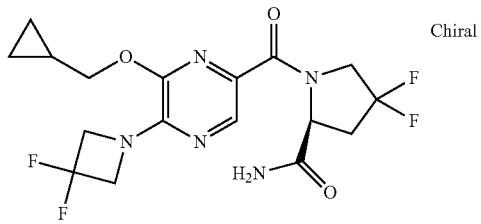 [SMILES: NC(=O)[C@@H]1CC(F)(F)CN1C(=O)c1cnc(N2CC(F)(F)C2)c(OCC2CC2)n1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and (2S)-4,4-difluoro-2-pyrrolidinecarboxamide hydrochloride (1:1) (CAN 426844-51-1; 36 mg, 0.19 mmol) as starting materials and isolated (29 mg, 40%) as off-white solid; LC-MS (UV peak area, ESI) 100%, 418.1504 [MH$^+$].

Example 20

[6-Cyclopropylmethoxy-5-(3,3-difluoro-azetidin-1-yl)-pyrazin-2-yl]-[4-(2-hydroxy-ethyl)-piperazin-1-yl]-methanone

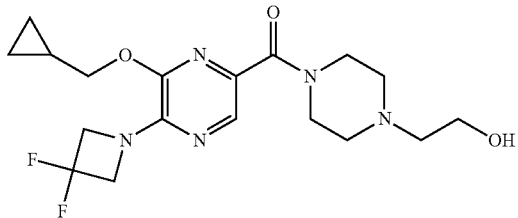 [SMILES: O=C(c1cnc(N2CC(F)(F)C2)c(OCC2CC2)n1)N1CCN(CCO)CC1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and 2-piperazin-1-yl-ethanol (CAN 103-76-4; 18.27 mg, 0.14 mmol) as starting materials and isolated (22 mg, 31.6%) as off white solid; LC-MS (UV peak area, ESI) 100%, 398.2 [MH$^+$].

Example 21

[6-Cyclopropylmethoxy-5-(3,3-difluoro-azetidin-1-yl)-pyrazin-2-yl]-(2,2-dimethyl-pyrrolidin-1-yl)-methanone

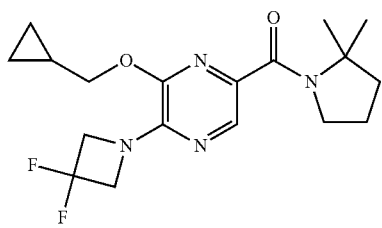 [SMILES: CC1(C)CCCN1C(=O)c1cnc(N2CC(F)(F)C2)c(OCC2CC2)n1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and 2,2-dimethylpyrrolidine (CAN 35018-15-6; 15 mg, 0.17 mmol) as starting materials and isolated (42 mg, 65.6%) as off white solid; LC-MS (UV peak area, ESI) 99.5%, 367.2 [MH]$^+$.

Example 22

(R)-1-[6-Cyclopropylmethoxy-5-(3,3-difluoro-azetidin-1-yl)-pyrazine-2-carbonyl]-pyrrolidine-2-carboxylic acid methyl ester

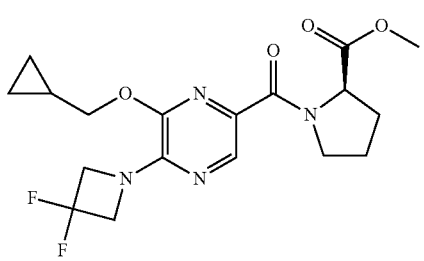 [SMILES: COC(=O)[C@H]1CCCN1C(=O)c1cnc(N2CC(F)(F)C2)c(OCC2CC2)n1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and (R)-pyrrolidine-2-carboxylic acid methyl ester (CAN 2577-48-2; 22 mg, 0.17 mmol) as starting materials and isolated (32 mg, 46.3%) as off white solid; LC-MS (UV peak area, ESI) 100%, 397.2 [MH$^+$].

Example 23

4-[6-Cyclopropylmethoxy-5-(3,3-difluoro-azetidin-1-yl)-pyrazine-2-carbonyl]-morpholin-2-one

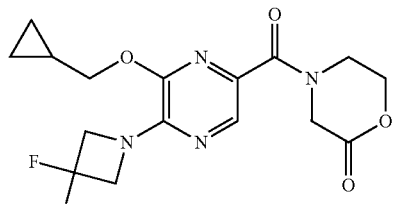

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and morpholine-2-one (CAN 4441-15-0; 18 mg, 0.17 mmol) as starting materials and isolated (4 mg, 4.68%) as off white solid; LC-MS (UV peak area, ESI) 100%, 369.2 [MH$^+$].

Example 24

(R)-1-[6-Cyclopropylmethoxy-5-(3,3-difluoro-azetidin-1-yl)-pyrazine-2-carbonyl]-pyrrolidine-2-carbothioic acid dimethylamide

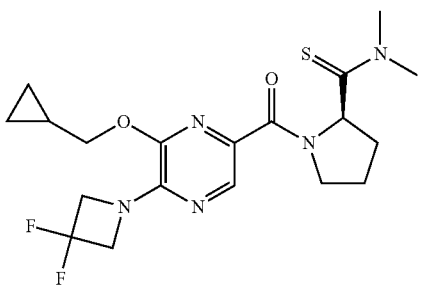 [SMILES: CN(C)C(=S)[C@H]1CCCN1C(=O)c1cnc(N2CC(F)(F)C2)c(OCC2CC2)n1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and (R)-pyrrolidine-2-carbothioic acid dimethylamide (27 mg, 0.17 mmol) as starting materials and isolated (19 mg, 25.6%) as off white solid; LC-MS (UV peak area, ESI) 100%, 426.2 [MH$^+$].

Example 25

Acetic acid 1-(5-cyclopropyl-6-cyclopropyl-methoxy-pyrazine-2-carbonyl)-3-methyl-pyrrolidin-3-yl ester

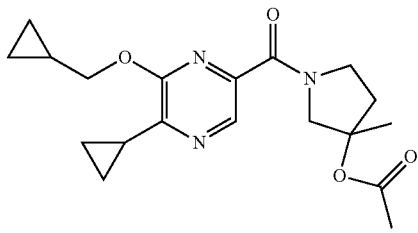 [SMILES: CC(=O)OC1(C)CCN(C(=O)c2cnc(C3CC3)c(OCC3CC3)n2)C1]

The title compound was synthesized in analogy to Example 1h, using 5-cyclopropyl-6-cyclopropylmethoxy-pyrazine-2-carboxylic acid (Example 1g, 50 mg, 0.21 mmol) and acetic acid 3-methyl-pyrrolidin-3-yl ester (30 mg, 0.21 mmol) as starting materials and isolated (30 mg, 40%) as off white sticky solid; LC-MS (UV peak area, ESI) 100%, 359.8 [MH+].

Example 26

(5-Cyclopropyl-6-cyclopropylmethoxy-pyrazin-2-yl)-(3,3,4,4-tetrafluoro-pyrrolidin-1-yl)-methanone

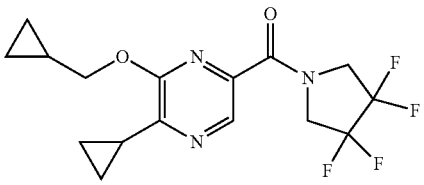 [SMILES: O=C(c1cnc(C2CC2)c(OCC2CC2)n1)N1CC(F)(F)C(F)(F)C1]

The title compound was synthesized in analogy to Example 1h, using 5-cyclopropyl-6-cyclopropylmethoxy-pyrazine-2-carboxylic acid (Example 1g, 50 mg, 0.21 mmol) and 3,3,4,4-tetrafluoro-pyrrolidine (CAN 1810-13-5; 30 mg, 0.21 mmol) as starting materials and isolated (50 mg, 65.8%) as off white sticky solid; LC-MS (UV peak area, ESI) 93.20%, 360.2 [MH+].

Example 27

Acetic acid (S)-1-[6-cyclopropylmethoxy-5-(3,3-difluoro-azetidin-1-yl)-pyrazine-2-carbonyl]-pyrrolidin-3-yl ester

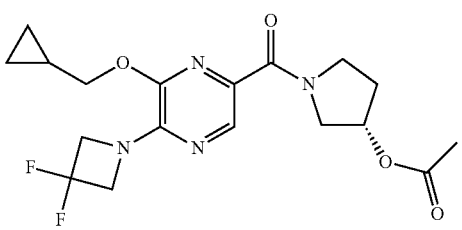 [SMILES: CC(=O)O[C@H]1CCN(C(=O)c2cnc(N3CC(F)(F)C3)c(OCC3CC3)n2)C1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and acetic acid (S)-pyrrolidin-3-yl ester (21.93 mg, 0.17 mmol) as starting materials and isolated (40 mg, 57.8%) as off white sticky solid; LC-MS (UV peak area, ESI) 100%, 397.0 [MH+].

Example 28

[6-Cyclopropylmethoxy-5-(3,3-difluoro-azetidin-1-yl)-pyrazin-2-yl]-(2-oxa-6-aza-spiro[3.4]oct-6-yl)-methanone

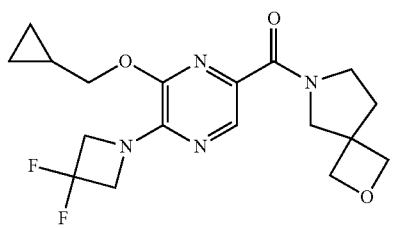 [SMILES: O=C(c1cnc(N2CC(F)(F)C2)c(OCC2CC2)n1)N1CCC2(COC2)C1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and 2-oxa-6-aza-spiro[3.4]octane (CAN 220290-68-6; 20 mg, 0.17 mmol) as starting materials and isolated (25 mg, 37.8%) as off white sticky solid; LC-MS (UV peak area, ESI) 99.8%, 381.0 [MH+].

Example 29

Acetic acid 1-[6-cyclopropylmethoxy-5-(3,3-difluoro-azetidin-1-yl)-pyrazine-2-carbonyl]-3-methyl-pyrrolidin-3-yl ester

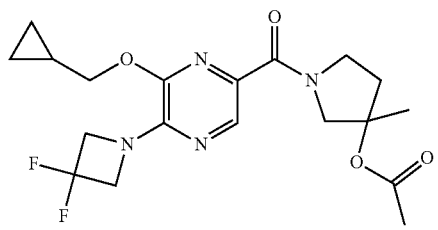 [SMILES: CC(=O)OC1(C)CCN(C(=O)c2cnc(N3CC(F)(F)C3)c(OCC3CC3)n2)C1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and acetic acid 3-methyl-pyrrolidin-3-yl ester (25 mg, 0.17 mmol) as starting materials and isolated (20 mg, 28.2%) as off white solid; LC-MS (UV peak area, ESI) 100%, 411.2 [MH+].

Example 30

[6-Cyclopropylmethoxy-5-(3,3-difluoro-azetidin-1-yl)-pyrazin-2-yl]-(3,3,4,4-tetrafluoro-pyrrolidin-1-yl)-methanone

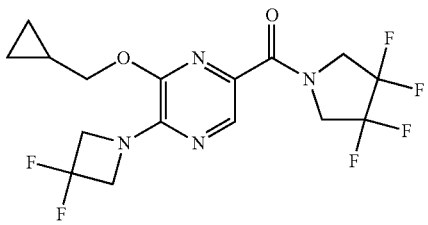 [SMILES: O=C(c1cnc(N2CC(F)(F)C2)c(OCC2CC2)n1)N1CC(F)(F)C(F)(F)C1]

The title compound was synthesized in analogy to Example 1h, using 6-cyclopropylmethoxy-5-(3,3-difluoro-azetidin-1-yl)-pyrazine-2-carboxylic acid (Example 2d, 50 mg, 0.17 mmol) and 3,3,4,4-tetrafluoro-pyrrolidine (CAN 1810-13-5; 30 mg, 0.21 mmol) as starting materials and isolated (45 mg, 60%) as off white solid; LC-MS (UV peak area, ESI) 99.4%, 411.4 [MH+].

Example 31

5-(3,3-Difluoro-azetidin-1-yl)-6-(2,2,2-trifluoro-ethoxy)-pyrazine-2-carboxylic acid tert-butyl-methyl-amide a) 5-(3,3-Difluoro-azetidin-1-yl)-6-(2,2,2-trifluoro-ethoxy)-pyrazine-2-carboxylic acid

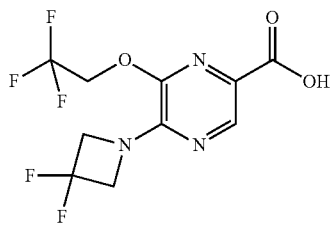 [SMILES: O=C(O)c1cnc(N2CC(F)(F)C2)c(OCC(F)(F)F)n1]

To a solution of 2,2,2-trifluoroethanol (0.496 mL, 6.8 mmol) in dry DMSO (12 mL) was added potassium hydroxide (0.668 g, 11.9 mmol) at ambient temperature followed by 6-bromo-5-(3,3-difluoro-azetidin-1-yl)-pyrazine-2-carboxylic acid (1.0 g, 3.4 mmol). The reaction mixture was stirred at ambient temperature for 1.5 hours. Water (100 mL) was added, the mixture was acidified with aqueous hydrochloric acid (10%, pH~3-4), and extracted with ethyl acetate. The organic phases were washed with water, combined, dried over Na$_2$SO$_4$, filtered and concentrated. The solid was crystallized from ethyl acetate by addition of heptane and dried in vacuo to give the title compound (0.96 g, 90.1%) as white crystalline solid; LC-MS (UV peak area, ESI) 91%, 312.0417 [M−H$^{-1}$].

b) 5-(3,3-Difluoro-azetidin-1-yl)-6-(2,2,2-trifluoro-ethoxy)-pyrazine-2-carboxylic acid tert-butyl-methyl-amide

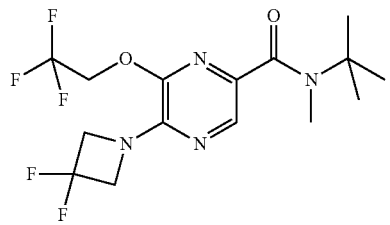 [SMILES: CN(C(=O)c1cnc(N2CC(F)(F)C2)c(OCC(F)(F)F)n1)C(C)(C)C]

The title compound was synthesized in analogy to Example 1h, using 5-(3,3-difluoro-azetidin-1-yl)-6-(2,2,2-trifluoro-ethoxy)-pyrazine-2-carboxylic acid (Example 31a, 40 mg, 0.128 mmol) and N,2-dimethyl-2-propanamine (CAN 14610-37-8; 16.9 µL, 0.140 mmol) as starting materials and isolated (48 mg, 98%) as white solid; LC-MS (UV peak area, ESI) 91%, 383.1519 [MH+].

Example 32

[5-(3,3-Difluoro-azetidin-1-yl)-6-(2,2,2-trifluoro-ethoxy)-pyrazin-2-yl]-(2,2-dimethyl-pyrrolidin-1-yl)-methanone

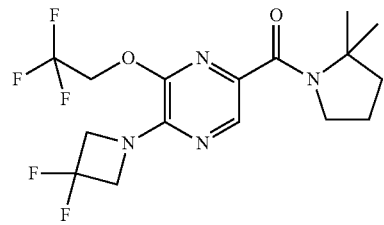 [SMILES: CC1(C)CCCN1C(=O)c1cnc(N2CC(F)(F)C2)c(OCC(F)(F)F)n1]

The title compound was synthesized in analogy to Example 1h, using 5-(3,3-difluoro-azetidin-1-yl)-6-(2,2,2-trifluoro-ethoxy)-pyrazine-2-carboxylic acid (Example 31a, 40 mg, 0.128 mmol) and 2,2-dimethylpyrrolidine (CAN 35018-15-6; 14 mg, 0.140 mmol) as starting materials and isolated (49 mg, 97%) as white solid; LC-MS (UV peak area, ESI) 91%, 395.1507 [MH]+.

Example 33

1-[6-Cyclopropylmethoxy-5-(3,3-difluoro-azetidin-1-yl)-pyrazine-2-carbonyl]-piperidine-2-carboxylic acid amide

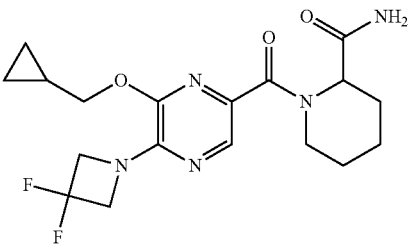

The title compound was synthesized in analogy to Example 1h, using 6-cyclopropylmethoxy-5-(3,3-difluoro-azetidin-1-yl)-pyrazine-2-carboxylic acid (Example 2d, 100 mg, 0.351 mmol) and 2-piperidinecarboxamide (CAN 19889-77-1; 49.4 mg, 0.368 mmol) as starting materials and isolated (120 mg, 87%) as light yellow solid; LC-MS (UV peak area, ESI) 100%, 396.1851 [MH]+.

Example 34

1-(5-Cyclopropyl-6-cyclopropylmethoxy-pyrazine-2-carbonyl)-4,4-dimethyl-pyrrolidine-2-carboxylic acid amide a) 4,4-Dimethyl-pyrrolidine-1,2-dicarboxylic acid 1-tert-butylester

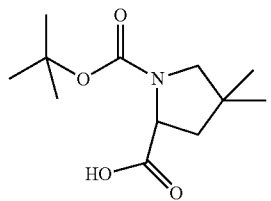 [SMILES: CC1(C)CC(C(=O)O)N(C(=O)OC(C)(C)C)C1]

To a solution of 4,4-dimethyl-proline (1.7 g, 11.8 mmol) in dry dioxane (29 mL) and water (24 mL) was added 1 N sodium hydroxide solution (9 mL) followed by slow addition of di-tert-butyldicarbonate (1.80 g, 8.2 mmol) dissolved in dioxane (5 mL) at ambient temperature. Additional 1 N sodium hydroxide solution (3 mL) was added and the mixture was stirred overnight. Additional di-tert-butyldicarbonate (1.80 g, 8.2 mmol) dissolved in dioxane (5 mL) was added and stirring continued for 3 hours. The mixture was concentrated, 1 N sodium bisulfite solution (22 mL) was added and the suspension was extracted with ethyl acetate. Organic phases were washed with water and brine, combined, dried over MgSO4, filtered and concentrated. The solid was crystallized from diethylether by addition of heptane and dried in vacuo to give the title compound (2.54 g, 89%) as white crystalline solid; MS (ESI) 242.0 [M−H−1].

b) 4,4-Dimethyl-pyrrolidine-1,2-dicarboxylic acid 1-tert-butyl ester 2-(2,5-dioxo-pyrrolidin-1-yl) ester

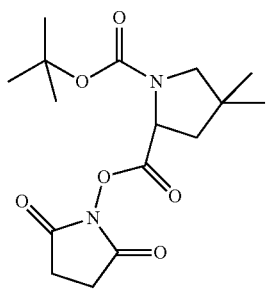 [SMILES: CC1(C)CC(C(=O)ON2C(=O)CCC2=O)N(C(=O)OC(C)(C)C)C1]

A solution of 4,4-dimethyl-pyrrolidine-1,2-dicarboxylic acid 1-tert-butylester (2.0 g, 8.22 mmol) in THF (20 mL) was cooled to 0° C. To the cold solution was added N-hydroxysuccinimide (1.2 g, 10.4 mmol) and diisopropylcarbodiimide (1.32 g, 10.4 mmol). Cooling was removed and the mixture stirred for 3 hours at room temperature. The urea was filtered off, washed with diethylether and the filtrates were concentrated. The residue was partitioned between ethyl acetate and cold water; organic phases were washed with cold brine, combined, dried with MgSO4, filtered and concentrated in vacuo. The residue was purified by flash chromatography (silica, heptane/ethyl acetate 9:1) to give the title compound (1.95 g, 70%) as colorless oil; MS (ESI) 341.1 [MH]+.

b) 2-Carbamoyl-4,4-dimethyl-pyrrolidine-1-carboxylic acid tert-butyl ester

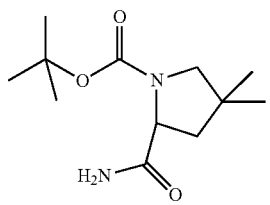

A solution of 4,4-dimethyl-pyrrolidine-1,2-dicarboxylic acid 1-tert-butyl ester 2-(2,5-dioxo-pyrrolidin-1-yl) ester (1.9 g, 5.58 mmol) in DCM (20 mL) was cooled to 0° C. Gaseous ammonia was bubbled for 15 minutes through the cold solution, and stirring was continued for 1 hour in the cold. The succinimide was filtered off, washed with DCM and the filtrates were partitioned between ethyl acetate and cold brine; organic phases were combined, dried with Na2SO4, filtered and concentrated in vacuo. The residue was purified by flash chromatography (silica, ethyl acetate) to give the title compound (1.33 g, 98%) as colorless foam; MS (ESI) 243.1 [MH+].

d) 4,4-Dimethyl-pyrrolidine-2-carboxylic acid amide hydrochloride

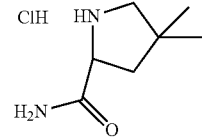

A solution of 2-carbamoyl-4,4-dimethyl-pyrrolidine-1-carboxylic acid tert-butyl ester (1.2 g, 4.95 mmol) in dioxane (5 mL) was cooled to 10° C. Hydrogen chloride dissolved in dioxane (10 mL, 6.4 N) was added and the mixture was stirred for 1.5 hours. Diethylether (50 mL) was added to completely precipitate the product, which was filtered and dried to give the title compound (0.84 g, 95%) as colorless solid; MS (ESI) 143.0 [MH+].

e) 1-(5-Cyclopropyl-6-cyclopropylmethoxy-pyrazine-2-carbonyl)-4,4-dimethyl-pyrrolidine-2-carboxylic acid amide

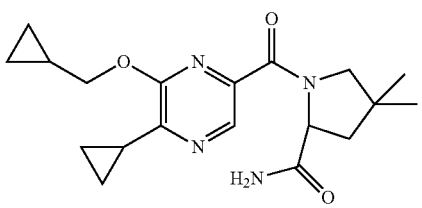 [SMILES: CC1(C)CC(C(N)=O)N(C(=O)c2cnc(C3CC3)c(OCC3CC3)n2)C1]

The title compound was synthesized in analogy to Example 1h, using 5-cyclopropyl-6-cyclopropylmethoxy-pyrazine-2-carboxylic acid (Example 1g, 100 mg, 0.427 mmol) and 4,4-dimethyl-pyrrolidine-2-carboxylic acid amide hydrochloride (Example 34d; 83.9 mg, 0.47 mmol) as starting materials and isolated (142 mg, 93%) as light yellow foam; LC-MS (UV peak area, ESI) 100%, 359.2085 [MH+].

Example 35

1-[6-Cyclopropylmethoxy-5-(3,3-difluoro-azetidin-1-yl)-pyrazine-2-carbonyl]-4,4-dimethyl-pyrrolidine-2-carboxylic acid amide

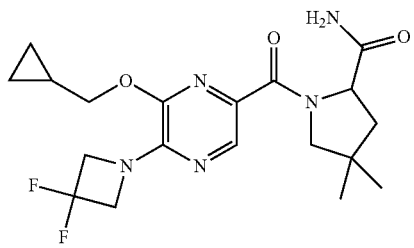 [SMILES: CC1(C)CC(C(N)=O)N(C(=O)c2cnc(N3CC(F)(F)C3)c(OCC3CC3)n2)C1]

The title compound was synthesized in analogy to Example 1h, using 6-cyclopropylmethoxy-5-(3,3-difluoro-azetidin-1-yl)-pyrazine-2-carboxylic acid (Example 2d, 100 mg, 0.351 mmol) and 4,4-dimethyl-pyrrolidine-2-carboxylic acid amide hydrochloride (Example 34d; 68.9 mg, 0.386 mmol) as starting materials and isolated (133 mg, 93%) as white foam; LC-MS (UV peak area, ESI) 100%, 410.2004 [MH+].

Example 36

(−)-1-[6-Cyclopropylmethoxy-5-(3,3-difluoro-azetidin-1-yl)-pyrazine-2-carbonyl]-piperidine-2-carboxylic acid amide

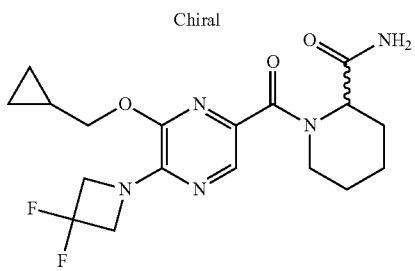 [SMILES: NC(=O)C1CCCCN1C(=O)c1cnc(N2CC(F)(F)C2)c(OCC2CC2)n1]

The enantiomers of 1-[6-cyclopropylmethoxy-5-(3,3-difluoro-azetidin-1-yl)-pyrazine-2-carbonyl]-piperidine-2-carboxylic acid amide (Example 33) were separated by chiral HPLC (Reprosil Chiral NR, 30% ethanol in n-heptane). The (−) enantiomer (48 mg, 44%) was isolated as white solid; LC-MS (UV peak area/ESI) 100%, 396.1842 [MH+]; (−) enantiomer, ~96% ee; $\alpha_D^{20}$ (MeOH)=−28.9°.

Example 37

(−)-4-[6-Cyclopropylmethoxy-5-(3,3-difluoro-azetidin-1-yl)-pyrazine-2-carbonyl]-thiomorpholine-3-carboxylic acid amide a) 4-[6-Cyclopropylmethoxy-5-(3,3-difluoro-azetidin-1-yl)-pyrazine-2-carbonyl]-thiomorpholine-3-carboxylic acid amide

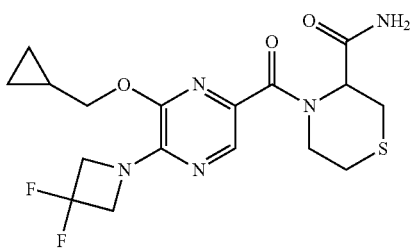 [SMILES: NC(=O)C1CSCCN1C(=O)c1cnc(N2CC(F)(F)C2)c(OCC2CC2)n1]

The title compound was synthesized in analogy to Example 1h, using 6-cyclopropylmethoxy-5-(3,3-difluoro-azetidin-1-yl)-pyrazine-2-carboxylic acid (Example 2d, 100 mg, 0.351 mmol) and 3-thiomorpholinecarboxamide (CAN 103742-31-0; 56.4 mg, 0.386 mmol) as starting materials and isolated (140 mg, 97%) as off-white solid; LC-MS (UV peak area, ESI) 100%, 414.1411 [MH+].

b) (−)-4-[6-Cyclopropylmethoxy-5-(3,3-difluoro-azetidin-1-yl)-pyrazine-2-carbonyl]-thiomorpholine-3-carboxylic acid amide

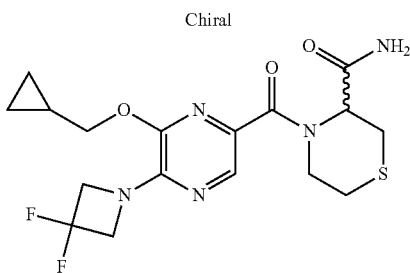 [SMILES: NC(=O)C1CSCCN1C(=O)c1cnc(N2CC(F)(F)C2)c(OCC2CC2)n1]

The enantiomers of 4-[6-cyclopropylmethoxy-5-(3,3-difluoro-azetidin-1-yl)-pyrazine-2-carbonyl]-thiomorpholine-3-carboxylic acid amide (Example 37a) were separated by chiral HPLC (Reprosil Chiral NR, 30% ethanol in n-heptane). The (−) enantiomer (48 mg, 39%) was isolated as light yellow solid; LC-MS (UV peak area/ESI) 100%, 414.1405 [MH+]; (−) enantiomer, ~100% ee; $\alpha_D^{20}$ (MeOH)=−42.4°.

Example 38

(−)-1-[6-Cyclopropylmethoxy-5-(3,3-difluoro-azetidin-1-yl)-pyrazine-2-carbonyl]-4,4-dimethyl-pyrrolidine-2-carboxylic acid amide

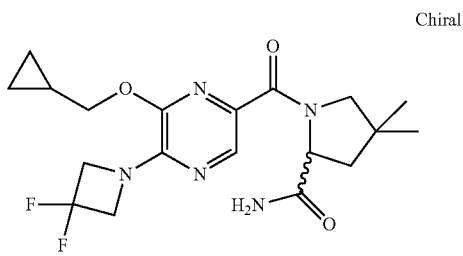 [SMILES: CC1(C)CC(C(N)=O)N(C(=O)c2cnc(N3CC(F)(F)C3)c(OCC3CC3)n2)C1]

The enantiomers of 1-[6-cyclopropylmethoxy-5-(3,3-difluoro-azetidin-1-yl)-pyrazine-2-carbonyl]-4,4-dimethyl-pyrrolidine-2-carboxylic acid amide (Example 35) were separated by chiral HPLC (Reprosil Chiral NR, 20% ethanol in n-heptane). The (−) enantiomer (52 mg, 44%) was isolated as white solid; LC-MS (UV peak area/ESI) 100%, 410.2003 [MH+]; (−) enantiomer, ~100% ee; $\alpha_D^{20}$ (MeOH)=−52.6°.

Example 39

(−)-1-(5-Cyclopropyl-6-cyclopropylmethoxy-pyrazine-2-carbonyl)-4,4-dimethyl-pyrrolidine-2-carboxylic acid amide

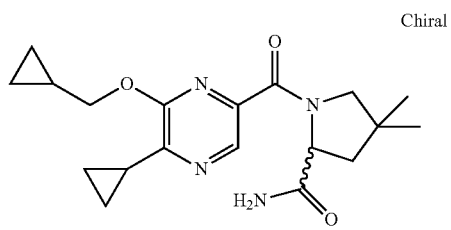 [SMILES: CC1(C)CC(C(N)=O)N(C(=O)c2cnc(C3CC3)c(OCC3CC3)n2)C1]
Chiral

The enantiomers of 1-(5-cyclopropyl-6-cyclopropylmethoxy-pyrazine-2-carbonyl)-4,4-dimethyl-pyrrolidine-2-carboxylic acid amide (Example 34e) were separated by chiral HPLC (Reprosil Chiral NR, 20% ethanol in n-heptane). The (−) enantiomer (52 mg, 41%) was isolated as white foam; LC-MS (UV peak area/ESI) 100%, 359.2082 [MH+]; (−) enantiomer, ~99% ee; $\alpha_D^{20}$ (MeOH)=−79.4°.

Example 40

(±)-5-[6-(Cyclopropylmethoxy)-5-(3,3-difluoroazetidin-1-yl)pyrazine-2-carbonyl]-5-azaspiro[2.4]heptane-6-carboxamide

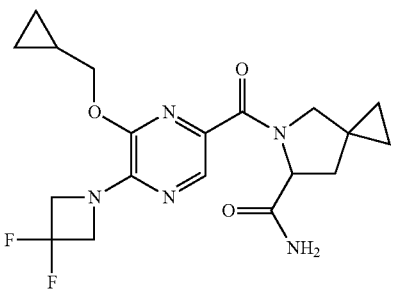 [SMILES: NC(=O)C1CC2(CC2)CN1C(=O)c1cnc(N2CC(F)(F)C2)c(OCC2CC2)n1]

a) (±)-tert-Butyl 6-carbamoyl-5-azaspiro[2.4]heptane-5-carboxylate

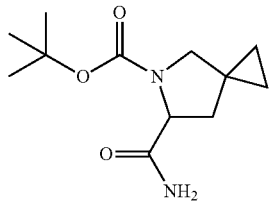 [SMILES: CC(C)(C)OC(=O)N1CC2(CC2)CC1C(N)=O]

Carbonyldiimidazole (211 mg, 1.3 mmol) was added to an ice cold solution of (±)-5-(tert-butoxycarbonyl)-5-azaspiro[2.4]heptane-6-carboxylic acid (CAN 1454843-77-6, 112 mg, 464 μmol) in DMF (1 mL). The reaction mixture was warmed to ambient temperature and stirring was continued for 2 h. Under ice cooling NH3 gas was bubbled for 10 min. through the reaction mixture. Stirring was continued at ambient temperature for 72 h. The reaction mixture was poured into 30 mL ice/water and extracted with EtOAc (2×30 mL). The combined extracts were washed with ice/brine (20 mL), dried over Na2SO4 and concentrated in vacuo to give the title compound (54 mg, 48%) as colorless oil which was used in the next reaction step without further purification, MS (ESI) 141.1 [MH-Boc+].

b) (±)-5-Azaspiro[2.4]heptane-6-carboxamide hydrochloride

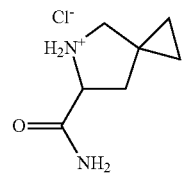

A solution of (±)-tert-butyl 6-carbamoyl-5-azaspiro[2.4]heptane-5-carboxylate (Example 40a, 65 mg, 270 μmol) in a 4 M solution of HCl in dioxane (1.4 mL) was stirred at ambient temperature for 4 h. The solvent was removed under reduced pressure to give the title compound (55 mg, quant.) as light yellow oil which was used in the next reaction step without further purification, LC-MS 141.1023 [MH+].

c) (±)-5-[6-(Cyclopropylmethoxy)-5-(3,3-difluoroazetidin-1-yl)pyrazine-2-carbonyl]-5-azaspiro[2.4]heptane-6-carboxamide 2-Bromo-1-ethylpyridinium tetrafluoroborate (38.3 mg, 119 μmol) was added to a solution of 6-(cyclopropylmethoxy)-5-(3,3-difluoroazetidin-1-yl)pyrazine-2-carboxylic acid (Example 2d, 20 mg, 70.1 μmol), (±)-5-azaspiro[2.4]heptane-6-carboxamide hydrochloride (Example 40b, 18.6 mg, 105 μmol) and DIEA (34.1 mg, 45.2 μL, 264 μmol) in dioxane (150 μL) under an argon atmosphere. The reaction mixture was stirred for 1 d at ambient temperature, poured onto ice/0.1 M NaOH (25 mL) and extracted with EtOAc (2×25 mL).

The combined extracts were washed with ice/0.1N HCl (25 mL) and icewater/brine (25 mL) to pH 6. The organic layers were dried over Na2SO4 and filtered off. The solvent was removed under reduced pressure and the crude product was purified by prep. HPLC (ACN/HCOOH 98/2%, Gemini NX 3u) to give the title compound (18 mg, 63%) as off-white solid, MS (ESI) 408.3 [MH+].

Example 41

(2S)-1-[6-(Cyclopropylmethoxy)-5-(3,3-difluoroazetidin-1-yl)pyrazine-2-carbonyl]-4-hydroxy-4-methyl-pyrrolidine-2-carboxamide

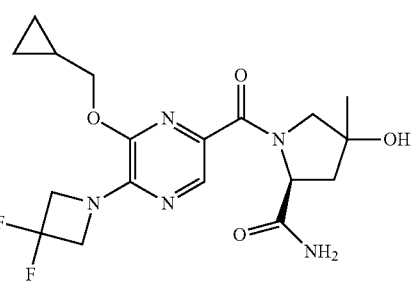

a) (2S)-Methyl 4-hydroxy-4-methylpyrrolidine-2-carboxylate hydrochloride

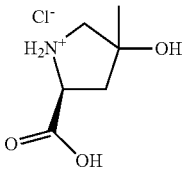

A solution of (2S)-1-tert-butyl 2-methyl 4-hydroxy-4-methylpyrrolidine-1,2-dicarboxylate (CAN 1367552-84-8, 466 mg, 1.8 mmol) in a 4 M solution of hydrogen chloride in dioxane (8.99 mL, 36 mmol) was stirred for 4 h at ambient temperature. The solvent was removed under reduced pressure to give the title compound (446 mg, quant.) as brown solid, which was used in the next reaction step without further purification, MS (ESI) 160.1 [MH$^+$].

b) (2S)-4-Hydroxy-4-methylpyrrolidine-2-carboxamide hydrochloride

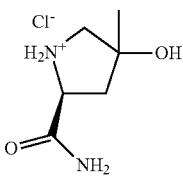

A solution of (2S)-methyl 4-hydroxy-4-methylpyrrolidine-2-carboxylate hydrochloride (Example 41a, 446 mg, 2.28 mmol) in a 7 M solution of ammonia in methanol (6.51 mL, 45.6 mmol) was stirred for 2 d at ambient temperature. The reaction mixture was poured onto icewater (30 mL) and extracted with EtOAc (2×40 mL). The aqueous layer was concentrated in vacuo. The residue was suspended in methanol and EtOAc. The solid was filtered off. After adding a 4 M solution of HCl in dioxane (2 mL) the filtrate was concentrated in vacuo to give the title compound (550 mg, quant.) as brown solid which was used in the next reaction step without further purification, MS (ESI) 144.1 [MH$^+$].

c) (2S)-1-[6-(Cyclopropylmethoxy)-5-(3,3-difluoroazetidin-1-yl)pyrazine-2-carbonyl]-4-hydroxy-4-methylpyrrolidine-2-carboxamide In analogy to the procedure described in Example 40c, 6-(cyclopropylmethoxy)-5-(3,3-difluoroazetidin-1-yl)pyrazine-2-carboxylic acid (Example 2d, 50 mg, 175 µmol) was reacted with (2S)-4-hydroxy-4-methylpyrrolidine-2-carboxamide hydrochloride (Example 41b, 31.7 mg, 175 µmol) to obtain the title compound (12 mg, 13%) as light yellow oil, MS (ESI) 412.3 [MH$^+$].

Example 42

(2S)-1-[5-(3,3-Difluoroazetidin-1-yl)-6-(2,2-difluoroethoxyl)pyrazine-2-carbonyl]-4,4-difluoro-pyrrolidine-2-carboxamide

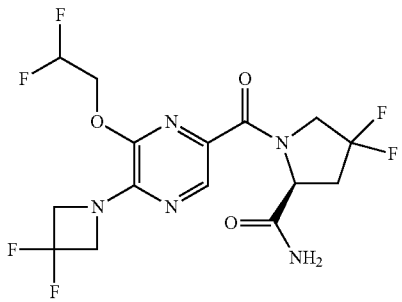 [SMILES: NC(=O)[C@@H]1CC(F)(F)CN1C(=O)c1cnc(N2CC(F)(F)C2)c(OCC(F)F)n1]

a) Methyl 5-(3,3-difluoroazetidin-1-yl)-6-(2,2-difluoroethoxyl)pyrazine-2-carboxylate

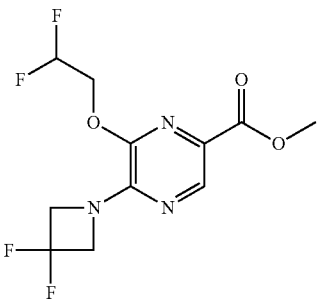 [SMILES: COC(=O)c1cnc(N2CC(F)(F)C2)c(OCC(F)F)n1]

Lithium 2-methylpropan-2-olate (3.39 mL, 7.47 mmol) was added within 30 minutes at ambient temperature to a solution of methyl 6-bromo-5-(3,3-difluoroazetidin-1-yl)pyrazine-2-carboxylate (CAN 1432507-18-0, 1 g, 3.25 mmol) and 2,2-difluoroethanol (CAN 359-13-7, 346 mg, 267 µL, 4.22 mmol) in DMF (6.67 mL). The reaction mixture was heated to 70° C. and stirred for 20 h. After cooling to ambient temperature, icewater (50 mL) and 2 N HCl (8 mL) were added. A brown precipitate formed which was filtered off and purified by column chromatography to obtain the title compound (77 mg, 7%) as light yellow solid; MS (ESI) m/e=310.1 [MH$^+$].

b) 5-(3,3-Difluoroazetidin-1-yl)-6-(2,2-difluoroethoxyl)pyrazine-2-carboxylic acid

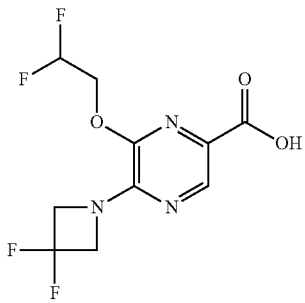 [SMILES: O=C(O)c1cnc(N2CC(F)(F)C2)c(OCC(F)F)n1]

A solution of methyl 5-(3,3-difluoroazetidin-1-yl)-6-(2,2-difluoroethoxyl)pyrazine-2-carboxylate (Example 42 a, 77 mg, 249 µmol) and lithium hydroxide hydrate (12.5 mg, 299 µmol) in tetrahydrofuran (500 µL) and water (50 µL) was stirred for 12 h at ambient temperature. The reaction mixture was poured onto ice/0.1 N HCl (1×25 mL) and extracted with EtOAc (2×25 mL). The combined extracts were washed with ice/brine (25 mL), dried over Na$_2$SO$_4$, filtered and evaporated to dryness to give the title compound (68 mg, 93%) as off-white solid; MS (ESI) m/e=296.1 [MH$^+$].

c) (2S)-1-[5-(3,3-Difluoroazetidin-1-yl)-6-(2,2-difluoroethoxyl)pyrazine-2-carbonyl]-4,4-difluoro-pyrrolidine-2-carboxamide 2-Bromo-1-ethylpyridinium tetrafluoroborate (46.2 mg, 144 µmol) was added to a solution of 5-(3,3-difluoro azetidin-1-yl)-6-(2,2-difluoroethoxy)pyrazine-2-carboxylic acid (Example 42 b, 25 mg, 84.7 µmol), (2S)-4,4-difluoro-2-pyrrolidinecarboxamide hydrochloride (CAN 426844-51-1, 19.0 mg, 102 µmol) and DIEA (41.0 mg, 54.4 µL, 318 µmol) in dioxane (500 µL). The reaction mixture was stirred for 1 d at ambient temperature, poured onto ice/0.1N HCl (1×25 mL) and extracted with EtOAc (2×25 mL). The combined extracts were washed with icewater/brine (1×25 mL), dried over Na$_2$SO$_4$, filtered off and evaporated in vacuo. The crude product was crystallized from EtOAc and heptane to obtain the title compound (19 mg, 53%) as off-white solid; MS (ESI) m/e=428.1161 [MH$^+$].

Example 43

Pharmacological tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM $MgCl_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 µM, more particularly of 1 nM to 3 µM and most particularly of 1 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. Using the cAMP-Nano-TRF detection kit the assay (Roche Diagnostics) was stopped by the addition of 50 µl lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P (T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

The compounds of the invention are CB2 agonists with $EC_{50}$ below 0.5 µM and selectivity versus CB1 in the corresponding assay of at least 10 fold. Particular compound of the invention are CB2 agonists with $EC_{50}$ below 0.05 µM and selectivity versus CB1 in the corresponding assay of at least 500 fold.

For example, the following compounds showed the following human $EC_{50}$ values in the functional cAMP assay described above:

| Example | human CB2 $EC_{50}$ [µM] | human CB1 $EC_{50}$ [µM] |
| --- | --- | --- |
| 1 | 0.0573 | >10 |
| 2 | 0.0049 | >10 |
| 3 | 0.004 | >10 |
| 4 | 0.0043 | >10 |
| 5 | 0.0817 | >10 |
| 6 | 0.2569 | >10 |
| 7 | 0.0032 | >10 |
| 8 | 0.0298 | >10 |
| 9 | 0.0199 | >10 |
| 10 | 0.015 | >10 |
| 11 | 0.0068 | >10 |
| 12 | 0.0092 | >10 |
| 13 | 0.0685 | >10 |
| 14 | 0.0146 | >10 |
| 15 | 0.0112 | >10 |
| 16 | 0.1907 | >10 |
| 17 | 0.1404 | >10 |
| 18 | 0.0235 | >10 |
| 19 | 0.0057 | >10 |
| 20 | 0.3157 | >10 |
| 21 | 0.0043 | >10 |
| 22 | 0.2524 | >10 |
| 23 | 0.0184 | >10 |
| 24 | 0.3331 | >10 |
| 25 | 0.1097 | >10 |
| 26 | 0.1236 | >10 |
| 27 | 0.2712 | >10 |
| 28 | 0.2041 | >10 |
| 29 | 0.0088 | >10 |
| 30 | 0.0263 | >10 |
| 31 | 0.1296 | >10 |
| 32 | 0.0812 | >10 |
| 33 | 0.3296 | >10 |
| 34 | 0.0016 | >10 |
| 35 | 0.0115 | >10 |
| 36 | 0.2167 | >10 |
| 37 | 0.3083 | >10 |
| 38 | 0.0014 | >10 |
| 39 | 0.0103 | >10 |
| 40 | 0.039 | >10 |
| 41 | 0.090 | >10 |
| 42 | 0.3097 | >10 |

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |

-continued

| Ingredients | Per tablet | |
|---|---|---|
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula (I)

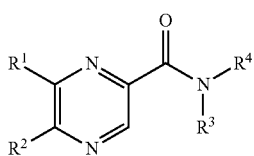

(I)

wherein
R$^1$ is cycloalkylalkoxy or haloalkoxy;
R$^2$ is cycloalkyl or haloazetidinyl;
R$^3$ and R$^4$ are independently selected from alkyl, alkoxy, alkoxyalkyl and alkoxycarbonylalkyl;
or R$^3$ and R$^4$ together with the nitrogen atom to which they are attached form heterocyclyl or substituted heterocyclyl, wherein heterocyclyl is pyrrolidinyl, morpholinyl, oxomorpholinyl, 2-oxo-5-aza-bicyclo[2.2.1]heptyl, 7-oxa-4-aza-spiro [2.5]octyl, piperazinyl, 2-oxa-6-aza-spiro[3.4]octyl, piperidinyl, or thiomorpholinyl, and wherein substituted heterocyclyl is heterocyclyl substituted with one to four substituents independently selected from alkyl, halogen, aminocarbonyl, hydroxyalkyl, alkoxycarbonyl, alkylthiocarbamoyl, and alkylcarbonyloxy;
or a pharmaceutically acceptable salt or ester thereof.

2. A compound according to claim 1, wherein R$^1$ is cycloalkylalkoxy.

3. A compound according to claim 1, wherein R$^1$ is cyclopropylmethoxy.

4. A compound according to claim 1, wherein R$^2$ is cyclopropyl or difluoroazetidinyl.

5. A compound according to claim 1, wherein R$^3$ and R$^4$ are independently selected from alkyl, alkoxy and alkoxyalkyl, or wherein R$^3$ and R$^4$ together with the nitrogen atom to which they are attached form heterocyclyl or substituted heterocyclyl, wherein heterocyclyl is pyrrolidinyl, or morpholinyl, and wherein substituted heterocyclyl is heterocyclyl substituted with one to three substituents independently selected from alkyl, halogen and aminocarbonyl.

6. A compound according to claim 1, wherein R$^3$ and R$^4$ are independently selected from methyl, tert-butyl, methoxyethyl or methoxybutyl, or wherein R$^3$ and R$^4$ together with the nitrogen atom to which they are attached form dimethylmorpholinyl, dimethylpyrrolidinyl, (aminocarbonyl)(difluoro)pyrrolidinyl, or (aminocarbonyl)(dimethyl)pyrrolidinyl.

7. A compound according to claim 1 selected from
(5-Cyclopropyl-6-cyclopropylmethoxy-pyrazin-2-yl)-((R)-2-methyl-pyrrolidin-1-yl)-methanone;
[6-Cyclopropylmethoxy-5-(3,3-difluoro-azetidin-1-yl)-pyrazin-2-yl]-((R)-2-methyl-pyrrolidin-1-yl)-methanone;
6-Cyclopropylmethoxy-5-(3,3-difluoro-azetidin-1-yl)-pyrazine-2-carboxylic acid tert-butyl-(2-methoxyethyl)-amide;
[6-Cyclopropylmethoxy-5-(3,3-difluoro-azetidin-1-yl)-pyrazin-2-yl]-(3,3-dimethyl-morpholin-4-yl)-methanone;
[6-Cyclopropylmethoxy-5-(3,3-difluoro-azetidin-1-yl)-pyrazin-2-yl]-((S)-2-methyl-pyrrolidin-1-yl)-methanone;
[6-Cyclopropylmethoxy-5-(3,3-difluoro-azetidin-1-yl)-pyrazin-2-yl]-(1R,4R)-2-oxa-5-aza-bicyclo[2.2.1]hept-5-yl-methanone;
6-Cyclopropylmethoxy-5-(3,3-difluoro-azetidin-1-yl)-pyrazine-2-carboxylic acid tert-butyl-methyl-amide;
[6-Cyclopropylmethoxy-5-(3,3-difluoro-azetidin-1-yl)-pyrazin-2-yl]-(3,3-difluoro-pyrrolidin-1-yl)-methanone;
6-Cyclopropylmethoxy-5-(3,3-difluoro-azetidin-1-yl)-pyrazine-2-carboxylic acid ethyl-isopropyl-amide;
[6-Cyclopropylmethoxy-5-(3,3-difluoro-azetidin-1-yl)-pyrazin-2-yl]-(7-oxa-4-aza-spiro[2.5]oct-4-yl)-methanone;
{tert-Butyl-[6-cyclopropylmethoxy-5-(3,3-difluoro-azetidin-1-yl)-pyrazine-2-carbonyl]-amino}-acetic acid ethyl ester;
6-Cyclopropylmethoxy-5-(3,3-difluoro-azetidin-1-yl)-pyrazine-2-carboxylic acid (2-methoxy-1,1-dimethylethyl)-methyl-amide;
[6-Cyclopropylmethoxy-5-(3,3-difluoro-azetidin-1-yl)-pyrazin-2-yl]-(2,2-dimethyl-morpholin-4-yl)-methanone;

5-Cyclopropyl-6-cyclopropylmethoxy-pyrazine-2-carboxylic acid (2-methoxy-1,1-dimethyl-ethyl)-methyl-amide;
(5-Cyclopropyl-6-cyclopropylmethoxy-pyrazin-2-yl)-(2,2-dimethyl-pyrrolidin-1-yl)-methanone;
(S)-1-(5-Cyclopropyl-6-cyclopropylmethoxy-pyrazine-2-carbonyl)-pyrrolidine-2-carboxylic acid methyl ester;
(5-Cyclopropyl-6-cyclopropylmethoxy-pyrazin-2-yl)-(7-oxa-4-aza-spiro[2.5]oct-4-yl)-methanone;
(S)-1-(5-Cyclopropyl-6-cyclopropylmethoxy-pyrazine-2-carbonyl)-4,4-difluoro-pyrrolidine-2-carboxylic acid amide;
(S)-1-[6-Cyclopropylmethoxy-5-(3,3-difluoro-azetidin-1-yl)-pyrazine-2-carbonyl]-4,4-difluoro-pyrrolidine-2-carboxylic acid amide;
[6-Cyclopropylmethoxy-5-(3,3-difluoro-azetidin-1-yl)-pyrazin-2-yl]-[4-(2-hydroxy-ethyl)-piperazin-1-yl]-methanone;
[6-Cyclopropylmethoxy-5-(3,3-difluoro-azetidin-1-yl)-pyrazin-2-yl]-(2,2-dimethyl-pyrrolidin-1-yl)-methanone;
(R)-1-[6-Cyclopropylmethoxy-5-(3,3-difluoro-azetidin-1-yl)-pyrazine-2-carbonyl]-pyrrolidine-2-carboxylic acid methyl ester;
4-[6-Cyclopropylmethoxy-5-(3,3-difluoro-azetidin-1-yl)-pyrazine-2-carbonyl]-morpholin-2-one;
(R)-1-[6-Cyclopropylmethoxy-5-(3,3-difluoro-azetidin-1-yl)-pyrazine-2-carbonyl]-pyrrolidine-2-carbothioic acid dimethylamide;
Acetic acid 1-(5-cyclopropyl-6-cyclopropylmethoxy-pyrazine-2-carbonyl)-3-methyl-pyrrolidin-3-yl ester;
(5-Cyclopropyl-6-cyclopropylmethoxy-pyrazin-2-yl)-(3,3,4,4-tetrafluoro-pyrrolidin-1-yl)-methanone;
Acetic acid (S)-1-[6-cyclopropylmethoxy-5-(3,3-difluoro-azetidin-1-yl)-pyrazine-2-carbonyl]-pyrrolidin-3-yl ester;
[6-Cyclopropylmethoxy-5-(3,3-difluoro-azetidin-1-yl)-pyrazin-2-yl]-(2-oxa-6-aza-spiro[3.4]oct-6-yl)-methanone;
Acetic acid 1-[6-cyclopropylmethoxy-5-(3,3-difluoro-azetidin-1-yl)-pyrazine-2-carbonyl]-3-methyl-pyrrolidin-3-yl ester;
[6-Cyclopropylmethoxy-5-(3,3-difluoro-azetidin-1-yl)-pyrazin-2-yl]-(3,3,4,4-tetrafluoro-pyrrolidin-1-yl)-methanone;
5-(3,3-Difluoro-azetidin-1-yl)-6-(2,2,2-trifluoro-ethoxy)-pyrazine-2-carboxylic acid tert-butyl-methyl-amide;
[5-(3,3-Difluoro-azetidin-1-yl)-6-(2,2,2-trifluoro-ethoxy)-pyrazin-2-yl]-(2,2-dimethyl-pyrrolidin-1-yl)-methanone;
1-[6-Cyclopropylmethoxy-5-(3,3-difluoro-azetidin-1-yl)-pyrazine-2-carbonyl]-piperidine-2-carboxylic acid amide;
1-(5-Cyclopropyl-6-cyclopropylmethoxy-pyrazine-2-carbonyl)-4,4-dimethyl-pyrrolidine-2-carboxylic acid amide;
1-[6-Cyclopropylmethoxy-5-(3,3-difluoro-azetidin-1-yl)-pyrazine-2-carbonyl]-4,4-dimethyl-pyrrolidine-2-carboxylic acid amide;
(−)-1-[6-Cyclopropylmethoxy-5-(3,3-difluoro-azetidin-1-yl)-pyrazine-2-carbonyl]-piperidine-2-carboxylic acid amide;
(−)-4-[6-Cyclopropylmethoxy-5-(3,3-difluoro-azetidin-1-yl)-pyrazine-2-carbonyl]-thiomorpholine-3-carboxylic acid amide;
(−)-1-[6-Cyclopropylmethoxy-5-(3,3-difluoro-azetidin-1-yl)-pyrazine-2-carbonyl]-4,4-dimethyl-pyrrolidine-2-carboxylic acid amide; and
(−)-1-(5-Cyclopropyl-6-cyclopropylmethoxy-pyrazine-2-carbonyl)-4,4-dimethyl-pyrrolidine-2-carboxylic acid amide.

8. A compound according to claim 1 selected from

6-Cyclopropylmethoxy-5-(3,3-difluoro-azetidin-1-yl)-pyrazine-2-carboxylic acid tert-butyl-(2-methoxy-ethyl)-amide;
[6-Cyclopropylmethoxy-5-(3,3-difluoro-azetidin-1-yl)-pyrazin-2-yl]-(3,3-dimethyl-morpholin-4-yl)-methanone;
6-Cyclopropylmethoxy-5-(3,3-difluoro-azetidin-1-yl)-pyrazine-2-carboxylic acid tert-butyl-methyl-amide;
6-Cyclopropylmethoxy-5-(3,3-difluoro-azetidin-1-yl)-pyrazine-2-carboxylic acid (2-methoxy-1,1-dimethyl-ethyl)-methyl-amide;
(5-Cyclopropyl-6-cyclopropylmethoxy-pyrazin-2-yl)-(2,2-dimethyl-pyrrolidin-1-yl)-methanone;
(S)-1-[6-Cyclopropylmethoxy-5-(3,3-difluoro-azetidin-1-yl)-pyrazine-2-carbonyl]-4,4-difluoro-pyrrolidine-2-carboxylic acid amide;
[6-Cyclopropylmethoxy-5-(3,3-difluoro-azetidin-1-yl)-pyrazin-2-yl]-(2,2-dimethyl-pyrrolidin-1-yl)-methanone;
1-(5-Cyclopropyl-6-cyclopropylmethoxy-pyrazine-2-carbonyl)-4,4-dimethyl-pyrrolidine-2-carboxylic acid amide; and
(−)-1-[6-Cyclopropylmethoxy-5-(3,3-difluoro-azetidin-1-yl)-pyrazine-2-carbonyl]-4,4-dimethyl-pyrrolidine-2-carboxylic acid amide.

9. A process for the preparation of a compound according to claim 1 comprising the reaction of a compound of formula (II)

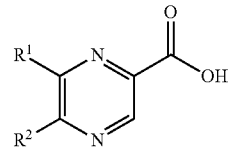

in the presence of $NHR^3R^4$, an amide coupling agent and a base, wherein $R^1$ to $R^4$ are as defined in claim 1.

10. A pharmaceutical composition comprising a compound of claim 1 and a therapeutically inert carrier.

* * * * *